US009157105B2

(12) United States Patent
Schoenhofen et al.

(10) Patent No.: US 9,157,105 B2
(45) Date of Patent: Oct. 13, 2015

(54) BIOSYNTHESIS OF CMP-LEGIONAMINIC ACID FROM FRUCTOSE-6-P, AND RESPECTIVE PATHWAY INTERMEDIATES, USING NOVEL GDP-LINKED PRECURSORS

(75) Inventors: Ian C. Schoenhofen, Ottawa (CA); Susan M. Logan, Ottawa (CA)

(73) Assignee: National Research Council of Canada, Ottawa (CA)

( * ) Notice: Subject to any disclaimer, the term of this patent is extended or adjusted under 35 U.S.C. 154(b) by 666 days.

(21) Appl. No.: 13/140,222

(22) PCT Filed: Dec. 16, 2009

(86) PCT No.: PCT/CA2009/001800
§ 371 (c)(1),
(2), (4) Date: Oct. 7, 2011

(87) PCT Pub. No.: WO2010/069047
PCT Pub. Date: Jun. 24, 2010

(65) Prior Publication Data
US 2012/0052532 A1    Mar. 1, 2012

Related U.S. Application Data

(60) Provisional application No. 61/122,973, filed on Dec. 16, 2008.

(51) Int. Cl.
*C12P 19/30*    (2006.01)
*C12N 9/90*    (2006.01)
*C12N 9/10*    (2006.01)
*C12N 9/12*    (2006.01)
*C12N 15/52*    (2006.01)
*C12P 19/28*    (2006.01)
*C12P 19/32*    (2006.01)

(52) U.S. Cl.
CPC .............. *C12P 19/305* (2013.01); *C12N 9/1048* (2013.01); *C12N 9/12* (2013.01); *C12N 9/90* (2013.01); *C12N 15/52* (2013.01); *C12P 19/28* (2013.01); *C12P 19/32* (2013.01)

(58) Field of Classification Search
CPC ........ C12P 19/32; C12P 19/305; C12P 19/28; C12N 9/1048; C12N 9/12; C12N 9/90
USPC .............................. 435/92, 94, 97
See application file for complete search history.

(56) References Cited

PUBLICATIONS

McNally et al. Journal of Biological Chemistry (2007) 282: 14463-14475.*
Schoenhofen et al: "Functional charaterization of dehydratase/aminotransferase pairs from Helicobater and Campylobacter—enzymes distinguishing the pseudaminic and bacillosamine biosynthetic pathways", The Journal of Biological Chemistry, vol. 281, 2006, pp. 723-732, XP002677812.
Schoenhofen et al: "Elucidation of the CMP-pseudaminic acid pathway in Helicobator pylori: synthesis from UDP-N-acetylglucosamine by a single enzymatic reaction", Glycobiology, vol. 16, 2006, pp. 8C-16C, XP002677921.
Kneidinger et al: "Biosynthesis of 2-acetamido-2, 6-dideoxy-L-hexoses in bacteria follows a pattern distinct from those of the pathways of 6-deoxy-L-hexoses", Biochemical Journal, vol. 371, 2003, pp. 989-995, XP002677813.
Morrison et al: "Mechanistic studies on PseB of pseudaminic acid biosynthesis: A UDP-N-acetylglucosamine 5-inverting 4, 6-dehydratase", Bioorganic Chemistry, vol. 36, Oct. 7, 2008, pp. 312-320, XP025585294.
King et al: "The Structural basis for catalytic function of GMD and RMD, two closely related enzymes from the GDP-D-rhamnose biosynthesis pathway", Febs Journal, vol. 276,Mar. 30, 2009, pp. 2686-2700, XP002677814.
"Biosynthesis of CMP-N,N'-Diacetyllegionaminic Acid from UDP-N,N'-Diacetylbacillosamine in Legionella pneumophila", Pavel A. Glaze et al. 2008 American Chemical Society, Published on Web Feb. 15, 2008.
Parkhill, J., et al. (2000) The genome sequence of the food-borne pathogen Campylobacter jejuni reveals hypervariable sequences. Nature. 403:665-668.
Twine, S.M., et al (2008) Flagellar glycosylation in Clostridium botulinum. FEBS Journal. 275:4428-4444.

* cited by examiner

*Primary Examiner* — Susan Hanley
(74) *Attorney, Agent, or Firm* — Malcolm K. McGowan; Cermak Nakajima & McGowan LLP

(57) ABSTRACT

The sialic acid-like sugar legionaminic acid is found as a virulence-associated surface glyco-conjugate in *Legionella pneumophila* and *Campylobacter coli*. In this work, we have purified and biochemically characterized eleven candidate biosynthetic enzymes from *C. jejuni*, thereby fully reconstituting the biosynthesis of legionaminic acid and its CMP-activated form, starting from fructose-6-P. This pathway involves unique GDP-linked intermediates and provides a facile means for the efficient large-scale synthesis of an important sialic acid mimic and novel precursors.

23 Claims, 21 Drawing Sheets

| 1 | 2 | 3 | 4 | 5 | 6 | |
|---|---|---|---|---|---|---|
| 6.71 | | 4.29 | 3.89 | 4.10 | 1.29 | $\delta_H$ (ppm) |
| | | 68.2 | 56.0 | 75.5 | 17.4 | $\delta_C$ (ppm) |

BIOSYNTHESIS OF CMP-LEGIONAMINIC ACID FROM FRUCTOSE-6-P, AND RESPECTIVE PATHWAY INTERMEDIATES, USING NOVEL GDP-LINKED PRECURSORS

PRIOR APPLICATION INFORMATION

This application claims the benefit of U.S. Provisional Patent Application 61/122,973, filed Dec. 16, 2008.

BACKGROUND OF THE INVENTION

The sialic acids are a diverse family of α-keto sugars, sharing a defining 9-carbon structural skeleton, and are typically the outermost moiety of oligosaccharides on vertebrate glycolipids and glycoproteins. They are generally attached to the underlying sugar chain via an α-glycosidic linkage between their 2-position (FIG. 1) and either the 3- or 6-hydroxyl group of galactose or N-acetylgalactosamine, the 6-hydroxyl group of N-acetylglucosamine, or they may also exist as α2,8-linked homopolymers (Lehman et al., 2006). With the presence of various substitutions at their 4, 5, 7, 8 and 9 positions (Varki and Varki, 2007), their various linkages, as well as their prominent and accessible location, it is not surprising this diverse family of sugars mediates and/or modulates a multitude of cellular interactions. Intercellular adhesion and signaling often results from sialic acid-specific binding proteins, or lectins, present on mammalian cell surfaces, most noted for their importance in regulating the immune system and in neuronal development. For example, the Siglecs (Sia-recognizing Ig-superfamily lectins) MAG and CD22 are involved in the binding of glial cells to gangliosides, which is critical to the long-term stability of myelin as well as inhibition of neurite outgrowth, and in negatively regulating B-cell function, respectively (Varki and Angata, 2006; Crocker et al., 2007; Varki, 2007). In addition, the neural cell adhesion molecule (NCAM) possesses α2,8-linked poly-sialic acid, which is important for brain development and neural regeneration, while its expression correlates with poor prognosis for several neuroendocrine tumours (Bork et al., 2007). Another example of sialic acid having prognostic significance in human cancer is the enhanced expression of α2,6-linked sialic acid on N-glycans, correlating with cancer progression, metastatic spread and poor prognosis for colon, breast and cervical cancers, to name a few (Hedlund et al., 2008).

It is possible that the importance of sialic acids within humans has contributed to the abundance of pathogens that display, bind or catabolize sialic acid. In fact, sialic acids are now recognized as the receptor or ligand most frequently used by pathogenic viruses, bacteria, and protozoa (Lehman et al., 2006). Furthermore, pathogenic bacteria have gained the ability to display sialic acids on their surface, either by de novo synthesis or through specific scavenging mechanisms, which is believed to influence pathogenesis through immune evasion, adhesion and invasion (Hsu et al., 2006; Severi et al., 2007). For example, the poly-sialic acid capsules of *Neisseria meningitidis* B and *Escherichia coli* K1 are poorly immunogenic, likely due to their molecular mimicry with the poly-sialic acid found on NCAM. In addition to utilizing host sialic acids as nutrient sources, many pathogenic bacteria possess sialic acid-specific lectins, which assist host-pathogen interactions and ultimately pathogenesis. Interestingly, they may also deploy soluble lectins, or toxins, that bind sialoglycoconjugates, such as the $AB_5$ cholera toxin that recognizes the GM1 ganglioside (Angstrom et al., 1994; Merrit et al., 1998), and pertussis toxin that recognizes the GD1a ganglioside (Hausman and Burns, 1993; Stein et al., 1994). Finally, an increasing number of protozoal pathogens have been found to utilize sialic acid-specific lectins, such as *Plasmodium* spp., the causative agent of malaria (Lehman et al., 2006). Moreover, Trypanosomes possess a cell-surface trans-sialidase allowing these organisms to coat themselves with mammalian derived sialic acid (Pontes de Carvalho et al., 1993).

In addition to presenting sialic acids on their surface, bacteria can also incorporate sialic acid-like sugars (5,7-diacetamido-3,5,7,9-tetradeoxy-nonulosonate derivatives) into their virulence-associated cell-surface glycoconjugates, such as lipopolysaccharide (LPS), capsular polysaccharide, pili and flagella (Schoenhofen et al., 2006b). These sugars (FIG. 1) are unique to microorganisms and may exhibit configurational differences compared with sialic acid. One particular sialic acid-like sugar, legionaminic acid (5,7-diacetamido-3,5,7,9-tetradeoxy-D-glycero-D-galacto-nonulosonic acid; X), has the same absolute configuration as sialic acid. Legionaminic acid was first identified in 1994 to be a component of *Legionella pneumophila* serogroup 1 LPS, hence its name (Knirel at al., 1994). However, it wasn't until 2001 that its correct stereochemistry was realized using synthetic methods (Tsvetkov et al., 2001). *L. pneumophila*, the causative agent of Legionnaires' disease, invades and replicates within alveolar macrophages leading to a debilitating and sometimes fatal pneumonia (Kooistra et al., 2002). The role of legionaminic acid in this disease progression may be significant, as it has been suggested that LPS is a key determinant in the ability of *L. pneumophila* to inhibit the fusion of phagosomes with lysosomes (Fernandez-Moreira et al., 2006). *L. pneumophila* serogroup 1 LPS contains both legionaminic acid and its 4-epimer isomer 4-epi-legionaminic acid (FIG. 1), although the majority appears to be an α2,4-linked homopolymer of legionaminic acid (Knirel et al., 2003). Interestingly, the first report of a proteoglycan containing legionaminic acid (X) was the recent discovery of this sugar on the flagellins of the gastrointestinal pathogen *Campylobacter coil* (McNally et al., 2007). Here, a number of Campylobacter genes were identified as being critical to its synthesis by screening isogenic mutants for the presence of CMP-legionaminic acid (XI) metabolites.

SUMMARY OF THE INVENTION

According to an aspect of the invention, there is provided a method of synthesis comprising:

(a) providing a reaction vessel comprising guanosine diphosphate (GDP)-N-acetyl-glucosamine, LegB, LegC, an N-acetyltransferase, LegG, water, acetyl-CoA, pyridoxal-phosphate (PLP), nicotinamide adenine dinucleotide (NAD), and an amino donor;

(b) converting the GDP-N-acetyl-glucosamine to GDP-2-acetamido-2,6-dideoxy-α-D-xylo-hexos-4-ulose with the LegB (dehydratase) and NAD;

(c) converting the GDP-2-acetamido-2,6-dideoxy-α-D-xylo-hexos-4-ulose to GDP-4-amino-4,6-dideoxy-α-D-GlcNAc with the LegC, PLP and the amino donor;

(d) converting the GDP-4-amino-4,6-dideoxy-α-D-GlcNAc to GDP-2,4-diacetamido-2,4,6-trideoxy-α-D-Glc with the N-acetyltransferase and the acetyl-CoA;

(e) converting the GDP-2,4-diacetamido-2,4,6-trideoxy-α-D-Glc to 2,4-diacetamido-2,4,6-trideoxy-D-Man with the LegG and the water; and (f) recovering the 2,4-diacetamido-2,4,6-trideoxy-D-Man.

The amino donor may be any suitable amino donor, for example, L-glutamic acid or L-glutamine.

According to an aspect of the invention, there is provided a method of synthesis comprising:
(a) providing a reaction vessel comprising GDP-N-acetylglucosamine, LegB, LegC, an N-acetyltransferase, LegG, LegI, phosphoenol pyruvate (PEP), water, acetyl-CoA, pyridoxal-phosphate (PLP), nicotinamide adenine dinucleotide (NAD), and an amino donor;
(b) converting the GDP-N-acetyl-glucosamine to GDP-2-acetamido-2,6-dideoxy-α-D-xylo-hexos-4-ulose with the LegB (dehydratase) and NAD;
(c) converting the GDP-2-acetamido-2,6-dideoxy-α-D-xylo-hexos-4-ulose to GDP-4-amino-4,6-dideoxy-α-D-GlcNAc with the LegC, PLP and the amino donor
(d) converting the GDP-4-amino-4,6-dideoxy-α-D-GlcNAc to GDP-2,4-diacetamido-2,4,6-trideoxy-α-D-Glc with the N-acetyltransferase and the acetyl-CoA;
(e) converting the GDP-2,4-diacetamido-2,4,6-trideoxy-α-D-Glc to 2,4-diacetamido-2,4,6-trideoxy-D-Man with the LegG and the water;
(f) converting the 2,4-diacetamido-2,4,6-trideoxy-D-Man to legionaminic acid with the LegI and PEP; and
(g) recovering the legionaminic acid.

In some embodiments, pyruvate is used in place of PEP.

According to an aspect of the invention, there is provided a method of synthesis comprising:
(a) providing a reaction vessel comprising GDP-N-acetylglucosamine, LegB, LegC, an N-acetyltransferase, LegG, LegI, LegF, cytidine triphosphate (CTP), phosphoenol pyruvate (PEP), water, acetyl-CoA, pyridoxal phosphate (PLP), nicotinamide adenine dinucleotide (NAD), $Me^{2+}$ and an amino donor;
(b) converting the GDP-N-acetyl-glucosamine to GDP-2-acetamido-2,6-dideoxy-α-D-xylo-hexos-4-ulose with the LegB (dehydratase) and NAD;
(c) converting the GDP-2-acetamido-2,6-dideoxy-α-D-xylo-hexos-4-ulose to GDP-4-amino-4,6-dideoxy-α-D-GlcNAc with the LegC, PLP and the amino donor;
(d) converting the GDP-4-amino-4,6-dideoxy-α-D-GlcNAc to GDP-2,4-diacetamido-2,4,6-trideoxy-α-D-Glc with the N-acetyltransferase and the acetyl-CoA;
(e) converting the GDP-2,4-diacetamido-2,4,6-trideoxy-α-D-Glc to 2,4-diacetamido-2,4,6-trideoxy-D-Man with the LegG and the water;
(f) converting the 2,4-diacetamido-2,4,6-trideoxy-D-Man to legionaminic acid with the LegI and PEP;
(g) converting the legionaminic acid to CMP-legionaminic acid with the LegF, $Me^{2+}$ and the CTP; and
(h) recovering the CMP-legionaminic acid.

As used herein, '$Me^{2+}$' refers to any divalent cation, for example but by no means limited to $Mg^{2+}$, $Mn^{2+}$ and the like.

According to an aspect of the invention, there is provided a method of synthesis comprising:
(a) providing a reaction vessel comprising GDP-N-acetylglucosamine, LegB, LegC, an N-acetyltransferase, acetyl-CoA, phosphoenol pyruvate (PLP), nicotinamide adenine dinucleotide (NAD) and an amino donor;
(b) converting the GDP-N-acetyl-glucosamine to GDP-2-acetamido-2,6-dideoxy-α-D-xylo-hexos-4-ulose with the LegB (dehydratase) and NAD;
(c) converting the GDP-2-acetamido-2,6-dideoxy-α-D-xylo-hexos-4-ulose to GDP-4-amino-4,6-dideoxy-α-D-GlcNAc with the LegC, PLP and the amino donor;
(d) converting the GDP-4-amino-4,6-dideoxy-α-D-GlcNAc to GDP-2,4-diacetamido-2,4,6-trideoxy-α-D-Glc with the N-acetyltransferase and the acetyl-CoA; and
(e) recovering the GDP-2,4-diacetamido-2,4,6-trideoxy-α-D-Glc.

According to an aspect of the invention, there is provided a method of synthesis comprising:
(a) providing a reaction vessel comprising GDP-N-acetylglucosamine, LegB, LegC, pyridoxal-phosphate (PLP), nicotinamide adenine dinucleotide (NAD), and an amino donor;
(b) converting the GDP-N-acetyl-glucosamine to GDP-2-acetamido-2,6-dideoxy-α-D-xylo-hexos-4-ulose with the LegB (dehydratase) and NAD;
(c) converting the GDP-2-acetamido-2,6-dideoxy-α-D-xylo-hexos-4-ulose to GDP-4-amino-4,6-dideoxy-α-D-GlcNAc with the LegC, PLP and the amino donor; and
(d) recovering the GDP-4-amino-4,6-dideoxy-α-D-GlcNAc.

According to an aspect of the invention, there is provided a method of synthesis comprising:
(a) providing a reaction vessel comprising GDP-N-acetylglucosamine, nicotinamide adenine dinculeotide (NAD) and LegB;
(b) converting the GDP-N-acetyl-glucosamine to GDP-2-acetamido-2,6-dideoxy-α-D-xylo-hexos-4-ulose with the LegB (dehydratase) and NAD; and
(c) recovering the GDP-2-acetamido-2,6-dideoxy-α-D-xylo-hexos-4-ulose.

According to an aspect of the invention, there is provided a method of synthesis comprising:
(a) providing a reaction vessel comprising GDP-2-acetamido-2,6-dideoxy-α-D-xylo-hexos-4-ulose, LegC, an N-acetyltransferase, LegG, water, acetyl-CoA, pyridoxal-phosphate (PLP) and an amino donor;
(b) converting the GDP-2-acetamido-2,6-dideoxy-α-D-xylo-hexos-4-ulose to GDP-4-amino-4,6-dideoxy-α-D-GlcNAc with the LegC, PLP and the amino donor;
(c) converting the GDP-4-amino-4,6-dideoxy-α-D-GlcNAc to GDP-2,4-diacetamido-2,4,6-trideoxy-α-D-Glc with the N-acetyltransferase and the acetyl-CoA;
(d) converting the GDP-2,4-diacetamido-2,4,6-trideoxy-α-D-Glc to 2,4-diacetamido-2,4,6-trideoxy-D-Man with the LegG and the water; and
(e) recovering the 2,4-diacetamido-2,4,6-trideoxy-D-Man.

According to an aspect of the invention, there is provided a method of synthesis comprising:
(a) providing a reaction vessel comprising GDP-2-acetamido-2,6-dideoxy-α-D-xylo-hexos-4-ulose, LegC, an N-acetyltransferase, acetyl-CoA, pyridoxal-phosphate (PLP) and an amino donor;
(b) converting the GDP-2-acetamido-2,6-dideoxy-α-D-xylo-hexos-4-ulose to GDP-4-amino-4,6-dideoxy-α-D-GlcNAc with the LegC, PLP and the amino donor;
(c) converting the GDP-4-amino-4,6-dideoxy-α-D-GlcNAc to GDP-2,4-diacetamido-2,4,6-trideoxy-α-D-Glc with the N-acetyltransferase and the acetyl-CoA; and
(d) recovering the GDP-2,4-diacetamido-2,4,6-trideoxy-α-D-Glc.

According to an aspect of the invention, there is provided a method of synthesis comprising:
(a) providing a reaction vessel comprising GDP-2-acetamido-2,6-dideoxy-α-D-xylo-hexos-4-ulose, LegC, pyridoxal-phosphate (PLP) and an amino donor;
(b) converting the GDP-2-acetamido-2,6-dideoxy-α-D-xylo-hexos-4-ulose to GDP-4-amino-4,6-dideoxy-α-D-GlcNAc with the LegC, PLP and the amino donor; and
(c) recovering the GDP-4-amino-4,6-dideoxy-α-D-GlcNAc.

According to an aspect of the invention, there is provided a method of synthesis comprising:

(a) providing a reaction vessel comprising GDP-4-amino-4,6-dideoxy-α-D-GlcNAc, an N-acetyltransferase, and acetyl-CoA;

(b) converting the GDP-4-amino-4,6-dideoxy-α-D-GlcNAc to GDP-2,4-diacetamido-2,4,6-trideoxy-α-D-Glc with the N-acetyltransferase and the acetyl-CoA; and (c) recovering the GDP-2,4-diacetamido-2,4,6-trideoxy-α-D-Glc.

DESCRIPTION OF THE PREFERRED EMBODIMENTS

Figure 1:
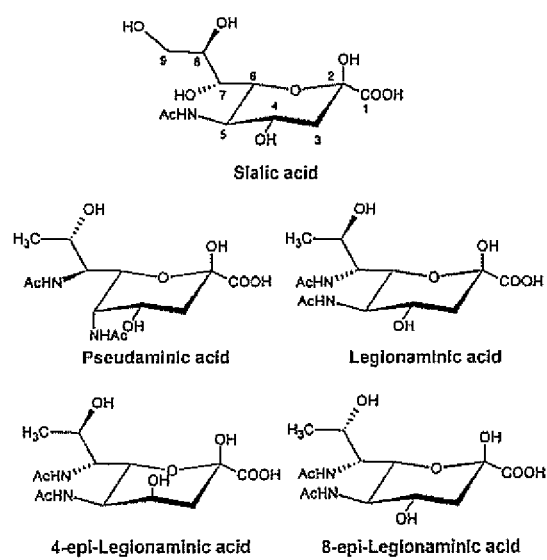
FIG. 1. Structures of sialic acid and sialic acid-like sugars. Sialic acid (Neu5Ac; D-glycero-D-galacto configuration), pseudaminic acid (Pse5Ac7Ac; L-glycero-L-manno configuration), legionaminic acid (Leg5Ac7Ac; D-glycero-D-galacto configuration), 4-epi-legionaminic acid (4eLeg5Ac7Ac; D-glycero-D-talo configuration), and 8-epi-legionaminic acid (8eLeg5Ac7Ac; L-glycero-D-galacto configuration) are shown. The thermodynamically more stable anomers, with equatorial carboxyl groups, are depicted. For reference, the 9 carbon atoms of sialic acid are numbered.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

The medically important sugar legionaminic acid is difficult to synthesize chemically; for example, using 2,4-diacetamido-2,4,6-trideoxy-D-Man and oxaloacetic acid results in yields of legionaminic acid of only 7%. However, using the methods described herein, substantially quantitative yields and in some embodiments essentially quantitative of legionaminic acid (X) and CMP-legionaminic acid (XI) may be obtained from GDP-GlcNAc in vitro and from fructose-6-P (I) in vivo. Also described is the involvement of unique GDP-linked intermediates as well as the biosynthetic enzymes PtmE, LegB, LegC, LegH and LegG resulting in greatly enhanced biosynthetic efficiencies. This method also allows for a superior production of 2,4-diacetamido-2,4,6-trideoxy-D-Man (IX), legionaminic acid (X)_and CMP-legionaminic acid (XI) as discussed below.

As discussed herein, enzymes in the synthesis pathways described herein are referred to by their Campylobacter designations (Table 2). However, as will be understood by one of skill in the art, there are other known species which produce legionaminic acid, for example but by no means limited to *Legionella, Clostridium, Campylobacter* and *Vibrio*. Accordingly, it is to be understood that the enzymes referred to herein refer to enzymatic activities, not necessarily the specific *Campylobacter* enzymes. For example, PtmF is an isomerase and PtmA is a glutaminase and PtmA/PtmF together are a glucosamine-6-phosphate synthase with isomerase and amidotransferase activities. Similarly, PgmL refers to a phosphoglucosamine mutase or phosphoglucomutase; PtmE refers to a NDP-sugar pyrophosphorylase or nucleotidyltransferase, and within the above-described pathways, it is specifically a glucosamine-1-phosphate guanylyltransferase; GlmU refers to a GDP-glucosamine N-acetyltransferase; LegB refers to a NAD-dependent GDP-N-acetyl-glucosamine 4,6-dehydratase; LegC refers to a PLP-dependent GDP-2-acetamido-2,6-dideoxy-α-D-xylo-hexos-4-ulose aminotransferase; LegH refers to a GDP-4-amino-4,6-dideoxy-α-D-GlcNAc N-acetyltransferase; LegG refers to a GDP-2,4-diacetamido-2,4,6-trideoxy-α-D-Glc hydrolyzing 2-epimerase; LegI refers to a legionaminic acid synthase; and LegF refers to a CMP-legionaminic acid synthetase. Accordingly, enzymes having similar activities from other organisms capable of legionaminic acid synthesis may be substituted therefor and are within the scope of the invention. It is of note that such suitable enzymes can be easily identified by one of skill in the art by a variety of means, for example, by searching any of a variety of databases using either keywords or relying on sequence homology. For example, the Cj numbers for Leg biosynthetic enzymes are the same for *Campylobacter jejuni* and *Campylobacter coli* organisms. In the *Clostridium botulinum* type F Langeland strain, the homologs are: PtmE—CLI_2778; LegB—CLI_2770; LegC—CLI_2769; LegG—CLI_2777; LegI—CLI_2775; LegF—CLI_2773.

According to an aspect of the invention, there is provided a method of synthesis comprising:

(a) providing a reaction vessel comprising GDP-N-acetyl-glucosamine, LegB, LegC, LegH, LegG, water, acetyl-CoA, pyridoxal-phosphate (PLP), nicotinamide adenine dinucleotide (NAD) and an amino donor;

(b) converting the GDP-N-acetyl-glucosamine to GDP-2-acetamido-2,6-dideoxy-α-D-xylo-hexos-4-ulose with the LegB (dehydratase) and NAD;

(c) converting the GDP-2-acetamido-2,6-dideoxy-α-D-xylo-hexos-4-ulose to GDP-4-amino-4,6-dideoxy-α-D-GlcNAc with the LegC, PLP and the amino donor;

(d) converting the GDP-4-amino-4,6-dideoxy-α-D-GlcNAc to GDP-2,4-diacetamido-2,4,6-trideoxy-α-D-Glc with the LegH and the acetyl-CoA;

(e) converting the GDP-2,4-diacetamido-2,4,6-trideoxy-α-D-Glc to 2,4-diacetamido-2,4,6-trideoxy-D-Man with the LegG and the water; and (f) recovering the 2,4-diacetamido-2,4,6-trideoxy-D-Man.

The amino donor may be any suitable amino donor, for example, L-glutamic acid or L-glutamine.

In some embodiments of the invention, prior to step (f), the 2,4-diacetamido-2,4,6-trideoxy-D-Man is converted to legionaminic acid with LegI in the presence of phosphoenol pyruvate (PEP) and the legionaminic acid is recovered. This additional step may be applied to other appropriate synthesis methods described herein.

In yet further embodiments of the invention, prior to recovery of the legionaminic acid, the legionaminic acid is converted to CMP-legionaminic acid with LegF in the presence of cytidine triphosphate (CTP) and $Me^{2+}$, and the CMP-legionaminic is recovered. This additional step may be applied to other appropriate synthesis methods described herein.

In some embodiments of the invention, prior to step (a), GDP-glucosamine is converted to GDP-N-acetyl-glucosamine with GlmU in the presence of acetyl-CoA. This additional step may be applied to other appropriate synthesis methods described herein.

It is noted that suitable uses for the recovered, that is purified or isolated 2,4-diacetamido-2,4,6-trideoxy-D-Man, legionaminic acid or CMP-legionaminic acid synthesized according to the methods described herein include but are by no means limited to the manufacture of pharmaceutical compositions for use as antivirals.

In other embodiments of the invention, prior to step (a), N-acetyl-glucosamine-1-phosphate is converted to NDP-N-acetyl-glucosamine with PtmE in the presence of nucleotide triphosphate (NTP), $Me^{2+}$ and a pyrophosphatase. Specifically, N-acetyl-glucosamine-1-phosphate, in the presence of GTP, CTP or TTP is converted to GDP-GlcNAc, CDP-GlcNAc and TDP-GlcNAc respectively This additional step may be applied to other appropriate synthesis methods described herein.

In some embodiments of the invention, prior to step (a), glucosamine-1-phosphate is converted to GDP-glucosamine with PtmE in the presence of guanosine triphosphate (GTP), $Me^{2+}$ and a pyrophosphatase. This additional step may be applied to other appropriate synthesis methods described herein.

In some embodiments of the invention, prior to step (a), glucosamine-6-phosphate is converted to glucosamine-1-phosphate with PgmL. This additional step may be applied to other appropriate synthesis methods described herein.

In some embodiments of the invention, prior to step (a), fructose-6-phosphate is converted to glucosamine-6-phosphate with PtmA and PtmF in the presence of a nitrogen donor. The nitrogen donor may be any suitable nitrogen donor, for example, L-glutamine (Gln) ammonia or L-asparagine (Asn). As will be appreciated by one of skill in the art, in some embodiments, for example certain in vitro embodiments, a reducing agent, for example but by no means limited to dithiothreotol (DTT), may be added. This additional step may be applied to other appropriate synthesis methods described herein.

According to an aspect of the invention, there is provided a method of synthesis comprising:

(a) providing a reaction vessel comprising GDP-N-acetyl-glucosamine, LegB, LegC, an N-acetyltransferase, LegG, water, acetyl-CoA, pyridoxal-phosphate (PLP), nicotinamide adenine dinucleotide (NAD) and an amino donor;

(b) converting the GDP-N-acetyl-glucosamine to GDP-2-acetamido-2,6-dideoxy-α-D-xylo-hexos-4-ulose with the LegB (dehydratase) and NAD;

(c) converting the GDP-2-acetamido-2,6-dideoxy-α-D-xylo-hexos-4-ulose to GDP-4-amino-4,6-dideoxy-α-D-GlcNAc with the LegC, PLP and the amino donor;

(d) converting the GDP-4-amino-4,6-dideoxy-α-D-GlcNAc to GDP-2,4-diacetamido-2,4,6-trideoxy-α-D-Glc with the N-acetyltransferase and the acetyl-CoA;

(e) converting the GDP-2,4-diacetamido-2,4,6-trideoxy-α-D-Glc to 2,4-diacetamido-2,4,6-trideoxy-D-Man with the LegG and the water; and (f) recovering the 2,4-diacetamido-2,4,6-trideoxy-D-Man.

In some embodiments of the invention, prior to step (f), the 2,4-diacetamido-2,4,6-trideoxy-D-Man is converted to legionaminic acid with LegI in the presence of phosphoenol pyruvate (PEP) and the legionaminic acid is recovered.

In yet further embodiments of the invention, prior to recovery of the legionaminic acid, the legionaminic acid is converted to CMP-legionaminic acid with LegF in the presence of cytidine triphosphate (CTP) and $Me^{2+}$, and the CMP-legionaminic is recovered.

According to an aspect of the invention, there is provided a method of synthesis comprising:

(a) providing a reaction vessel comprising GDP-N-acetyl-glucosamine, LegB, LegC, an N-acetyltransferase, LegG, LegI, phosphoenol pyruvate (PEP), water, acetyl-CoA, pyridoxal-phosphate (PLP), nicotinamide adenine dinucleotide (NAD) and an amino donor;

(b) converting the GDP-N-acetyl-glucosamine to GDP-2-acetamido-2,6-dideoxy-α-D-xylo-hexos-4-ulose with the LegB (dehydratase) and NAD;

(c) converting the GDP-2-acetamido-2,6-dideoxy-α-D-xylo-hexos-4-ulose to GDP-4-amino-4,6-dideoxy-α-D-GlcNAc with the LegC, PLP and the amino donor;

(d) converting the GDP-4-amino-4,6-dideoxy-α-D-GlcNAc to GDP-2,4-diacetamido-2,4,6-trideoxy-α-D-Glc with the N-acetyltransferase and the acetyl-CoA;

(e) converting the GDP-2,4-diacetamido-2,4,6-trideoxy-α-D-Glc to 2,4-diacetamido-2,4,6-trideoxy-D-Man with the LegG and the water;

(f) converting the 2,4-diacetamido-2,4,6-trideoxy-D-Man to legionaminic acid with the LegI and PEP; and (g) recovering the legionaminic acid.

In yet further embodiments of the invention, prior to step (g), the legionaminic acid is converted to CMP-legionaminic acid with LegF in the presence of CTP and $Me^{2+}$, and the CMP-legionaminic is recovered.

According to an aspect of the invention, there is provided a method of synthesis comprising:

(a) providing a reaction vessel comprising GDP-N-acetyl-glucosamine, LegB, LegC, an N-acetyltransferase, LegG, LegI, LegF, cytidine triphosphate (CTP), phosphoenol pyruvate (PEP), water, acetyl-CoA, pyridoxal-phosphate (PLP), nicotinamide adenine dinucleotide (NAD), Me$^{2+}$ and an amino donor;

(b) converting the GDP-N-acetyl-glucosamine to GDP-2-acetamido-2,6-dideoxy-α-D-xylo-hexos-4-ulose with the LegB (dehydratase) and NAD;

(c) converting the GDP-2-acetamido-2,6-dideoxy-α-D-xylo-hexos-4-ulose to GDP-4-amino-4,6-dideoxy-α-D-GlcNAc with the LegC, PLP and the amino donor;

(d) converting the GDP-4-amino-4,6-dideoxy-α-D-GlcNAc to GDP-2,4-diacetamido-2,4,6-trideoxy-α-D-Glc with the N-acetyltransferase and the acetyl-CoA;

(e) converting the GDP-2,4-diacetamido-2,4,6-trideoxy-α-D-Glc to 2,4-diacetamido-2,4,6-trideoxy-D-Man with the LegG and the water;

(f) converting the 2,4-diacetamido-2,4,6-trideoxy-D-Man to legionaminic acid with the LegI and PEP;

(g) converting the legionaminic acid to CMP-legionaminic acid with the LegF, Me$^{2+}$ and the CTP; and (h) recovering the CMP-legionaminic acid.

According to an aspect of the invention, there is provided a method of synthesis comprising:

(a) providing a reaction vessel comprising GDP-N-acetyl-glucosamine, LegB, LegC, an N-acetyltransferase, acetyl-CoA, pyridoxal-phosphate (PLP), nicotinamide adenine dinucleotide (NAD) and an amino donor;

(b) converting the GDP-N-acetyl-glucosamine to GDP-2-acetamido-2,6-dideoxy-α-D-xylo-hexos-4-ulose with the LegB (dehydratase) and NAD;

(c) converting the GDP-2-acetamido-2,6-dideoxy-α-D-xylo-hexos-4-ulose to GDP-4-amino-4,6-dideoxy-α-D-GlcNAc with the LegC, PLP and the amino donor; (d) converting the GDP-4-amino-4,6-dideoxy-α-D-GlcNAc to GDP-2,4-diacetamido-2,4,6-trideoxy-α-D-Glc with the N-acetyltransferase and the acetyl-CoA; and (e) recovering the GDP-2,4-diacetamido-2,4,6-trideoxy-α-D-Glc.

According to an aspect of the invention, there is provided a method of synthesis comprising:

(a) providing a reaction vessel comprising GDP-N-acetyl-glucosamine, LegB, LegC, pyridoxal-phosphate (PLP), nicotinamide adenine dinucleotide (NAD) and an amino donor;

(b) converting the GDP-N-acetyl-glucosamine to GDP-2-acetamido-2,6-dideoxy-α-D-xylo-hexos-4-ulose with the LegB (dehydratase) and NAD;

(c) converting the GDP-2-acetamido-2,6-dideoxy-α-D-xylo-hexos-4-ulose to GDP-4-amino-4,6-dideoxy-α-D-GlcNAc with the LegC, PLP and the amino donor; and (d) recovering the GDP-4-amino-4,6-dideoxy-α-D-GlcNAc.

According to an aspect of the invention, there is provided a method of synthesis comprising:

(a) providing a reaction vessel comprising GDP-N-acetyl-glucosamine, nicotinamide adenine dinucleotide (NAD) and LegB;

(b) converting the GDP-N-acetyl-glucosamine to GDP-2-acetamido-2,6-dideoxy-α-D-xylo-hexos-4-ulose with the LegB (dehydratase) and NAD;

(c) recovering the GDP-2-acetamido-2,6-dideoxy-α-D-xylo-hexos-4-ulose.

According to an aspect of the invention, there is provided a method of synthesis comprising:

(a) providing a reaction vessel comprising GDP-2-acetamido-2,6-dideoxy-α-D-xylo-hexos-4-ulose, LegC, an N-acetyltransferase, LegG, water, acetyl-CoA, pyridoxal-phosphate (PLP) and an amino donor;

(b) converting the GDP-2-acetamido-2,6-dideoxy-α-D-xylo-hexos-4-ulose to GDP-4-amino-4,6-dideoxy-α-D-GlcNAc with the LegC, PLP and the amino donor;

(c) converting the GDP-4-amino-4,6-dideoxy-α-D-GlcNAc to GDP-2,4-diacetamido-2,4,6-trideoxy-α-D-Glc with the N-acetyltransferase and the acetyl-CoA;

(d) converting the GDP-2,4-diacetamido-2,4,6-trideoxy-α-D-Glc to 2,4-diacetamido-2,4,6-trideoxy-D-Man with the LegG and the water; and (e) recovering the 2,4-diacetamido-2,4,6-trideoxy-D-Man.

According to an aspect of the invention, there is provided a method of synthesis comprising: (a) providing a reaction vessel comprising GDP-2-acetamido-2,6-dideoxy-α-D-xylo-hexos-4-ulose, LegC, an N-acetyltransferase, acetyl-CoA, pyridoxal-phosphate (PLP) and an amino donor;

(b) converting the GDP-2-acetamido-2,6-dideoxy-α-D-xylo-hexos-4-ulose to GDP-4-amino-4,6-dideoxy-α-D-GlcNAc with the LegC, PLP and the amino donor;

(c) converting the GDP-4-amino-4,6-dideoxy-α-D-GlcNAc to GDP-2,4-diacetamido-2,4,6-trideoxy-α-D-Glc with the N-acetyltransferase and the acetyl-CoA;

(d) recovering the GDP-2,4-diacetamido-2,4,6-trideoxy-α-D-Glc.

In another aspect of the invention, there is provided purified or isolated GDP-2,4-diacetamido-2,4,6-trideoxy-α-D-Glc. As used herein, 'isolated' means that the compound in question has been 'isolated', that is, removed, from its native environment. As used herein, 'purified' does not necessarily mean that the compound is at absolute purity but rather has been purified for example at least by 2 fold, 3 fold, 5 fold, 10 fold or the like. The GDP-2,4-diacetamido-2,4,6-trideoxy-α-D-Glc may be synthesized according to any one of the suitable methods described herein. It is noted that suitable uses for the purified or isolated GDP-2,4-diacetamido-2,4,6-trideoxy-α-D-Glc include but are by no means limited to the manufacture of pharmaceutical compositions for use as antivirals.

According to an aspect of the invention, there is provided a method of synthesis comprising:

(a) providing a reaction vessel comprising GDP-2-acetamido-2,6-dideoxy-α-D-xylo-hexos-4-ulose, LegC, pyridoxal-phosphate (PLP) and an amino donor;

(b) converting the GDP-2-acetamido-2,6-dideoxy-α-D-xylo-hexos-4-ulose to GDP-4-amino-4,6-dideoxy-α-D-GlcNAc with the LegC, PLP and the amino donor; and (c) recovering the GDP-4-amino-4,6-dideoxy-α-D-GlcNAc.

According to another aspect of the invention, there is provided purified or isolated GDP-4-amino-4,6-dideoxy-α-D-GlcNAc. The GDP-4-amino-4,6-dideoxy-α-D-GlcNAc may have been produced by any one of the methods described herein. It is noted that suitable uses for the purified or isolated GDP-4-amino-4,6-dideoxy-α-D-GlcNAc include but are by no means limited to the manufacture of pharmaceutical compositions for use as antivirals.

According to an aspect of the invention, there is provided a method of synthesis comprising:

(a) providing a reaction vessel comprising GDP-4-amino-4,6-dideoxy-α-D-GlcNAc, an N-acetyltransferase, and acetyl-CoA;

(b) converting the GDP-4-amino-4,6-dideoxy-α-D-GlcNAc to GDP-2,4-diacetamido-2,4,6-trideoxy-α-D-Glc with the N-acetyltransferase and the acetyl-CoA; and (c) recovering the GDP-2,4-diacetamido-2,4,6-trideoxy-α-D-Glc.

According to a further aspect of the invention, there is provided purified or isolated GDP-2,4-diacetamido-2,4,6- trideoxy-α-D-Glc. The GDP-2,4-diacetamido-2,4,6-trideoxy-α-D-Glc may have been prepared according to any one of the suitable methods described above.

According to an aspect of the invention, there is provided a method of synthesis comprising:

(a) providing a reaction vessel comprising GDP-N-acetyl-glucosamine, LegB, and nicotinamide adenine dinucleotide (NAD);

(b) converting the GDP-N-acetyl-glucosamine to GDP-2-acetamido-2,6-dideoxy-α-D-xylo-hexos-4-ulose with the LegB (dehydratase) and NAD; and (c) recovering the GDP-2-acetamido-2,6-dideoxy-α-D-xylo-hexos-4-ulose.

In another aspect of the invention, there is provided the use of LegB to convert GDP-N-acetyl-glucosamine to GDP-2-acetamido-2,6-dideoxy-α-D-xylo-hexos-4-ulose. Preferably, the use is carried out in vitro or in a recombinant host cell as discussed herein.

According to an aspect of the invention, there is provided a method of synthesis comprising: (a) providing a reaction vessel comprising GDP-2-acetamido-2,6-dideoxy-α-D-xylo-hexos-4-ulose, LegC, pyridoxal-phosphate (PLP) and an amino donor;

(b) converting the GDP-2-acetamido-2,6-dideoxy-α-D-xylo-hexos-4-ulose to GDP-4-amino-4,6-dideoxy-α-D-GlcNAc with the LegC, PLP and the amino donor; and (c) recovering the GDP-4-amino-4,6-dideoxy-α-D-GlcNAc.

In another aspect of the invention, there is provided the use of LegC to convert GDP-2-acetamido-2,6-dideoxy-α-D-xylo-hexos-4-ulose to GDP-4-amino-4,6-dideoxy-α-D-GlcNAc. Preferably, the use is carried out in vitro or in a recombinant host cell as discussed herein.

According to an aspect of the invention, there is provided a method of synthesis comprising:

(a) providing a reaction vessel comprising GDP-4-amino-4,6-dideoxy-α-D-GlcNAc, LegH, and acetyl-CoA;

(b) converting the GDP-4-amino-4,6-dideoxy-α-D-GlcNAc to GDP-2,4-diacetamido-2,4,6-trideoxy-α-D-Glc with LegH and the acetyl-CoA; and (c) recovering the GDP-2,4-diacetamido-2,4,6-trideoxy-α-D-Glc.

In another aspect of the invention, there is provided the use of LegH to convert GDP-4-amino-4,6-dideoxy-α-D-GlcNAc to GDP-2,4-diacetamido-2,4,6-trideoxy-α-D-Glc. Preferably, the use is carried out in vitro or in a recombinant host cell as discussed herein.

According to an aspect of the invention, there is provided a method of synthesis comprising:

(a) providing a reaction vessel comprising GDP-2,4-diacetamido-2,4,6-trideoxy-α-D-Glc, LegG, and water;

(b) converting the GDP-2,4-diacetamido-2,4,6-trideoxy-α-D-Glc to 2,4-diacetamido-2,4,6-trideoxy-D-Man with the LegG and the water; and (c) recovering the 2,4-diacetamido-2,4,6-trideoxy-D-Man.

In another aspect of the invention, there is provided the use of LegG to convert GDP-2,4-diacetamido-2,4,6-trideoxy-α-D-Glc to 2,4-diacetamido-2,4,6-trideoxy-D-Man. Preferably, the use is carried out in vitro or in a recombinant host cell as discussed herein.

In another aspect of the invention, there is provided the use of LegG to convert GDP-GlcNAc to ManNAc. Preferably, the use is carried out in vitro or in a recombinant host cell as discussed herein. Specifically, as used herein, a 'recombinant host cell' refers to a cell that does not normally express LegG or is a cell that has been modified for example via transfor-mation such that the LegG is overexpressed, that is, present at higher levels compared to a wild-type or control or untransformed cell.

In another aspect of the invention, there is provided a method of synthesis comprising: providing a reaction vessel comprising GDP-2,4-diacetamido-2,4,6-trideoxy-a-D-Glc, LegG and water and converting the GDP-2,4-diacetamido-2,4,6-trideoxy-a-D-Glc to 2,4-diacetamido-2,4,6-trideoxy-D-Man.

In a further aspect of the invention, there is provided a method of synthesis comprising providing a reaction vessel comprising GDP-2,4-diacetamido-2,4,6-trideoxy-a-D-Glc, LegG, water, LegI and phosphoenolpyruvate (PEP) and converting the GDP-2,4-diacetamido-2,4,6-trideoxy-a-D-Glc to legionaminic acid.

In a further aspect of the invention, there is provided a method of synthesis comprising providing a reaction vessel comprising GDP-2,4-diacetamido-2,4,6-trideoxy-a-D-Glc, LegG, water, LegI, phosphoenolpyruvate (PEP), LegF, cytidine triphosphate (CTP) and $Me^{2+}$ and converting the GDP-2,4-diacetamido-2,4,6-trideoxy-a-D-Glc, to CMP-legionaminic acid.

In some embodiments of the invention, the N-acetyltransferase refers to an enzyme such as for example LegH or PglD which carries out the N-acetylation reaction enzymatically or to chemical methods of acetylation which are well-known to one of skill in the art. Specifically, suitable chemical methods for acetylation of the compounds in question can be easily optimized with routine experimentation by one of skill in the art. As will be appreciated by one of skill in the art, substitutions of the enzymes listed above may be made provided that the replacing enzyme has sufficient substrate affinity such that the overall synthesis efficiency is not compromised to an undesirable extent.

As will be appreciated by one of skill in the art, the 'reaction vessel' may be an in vitro synthesis system or a recombinant host cell engineered to comprise the appropriate enzymes as listed above. In embodiments in which the synthesis is in vitro, the reaction vessel may further include or comprise a suitable reaction buffer as will be well known to those skilled in the biochemical arts. As will be appreciated by one of skill in the art, this may be done by engineering the host cell to express the non-native enzymes listed above for the synthesis method. The recombinant host cell may be prokaryotic or eukaryotic. In a preferred embodiment, the recombinant host cell is a bacterial cell, more preferably the recombinant host cell is of a bacterial strain that has UDP-GlcNAc utilizing pathways but does not normally produce the above-listed end products. In other embodiments, there is provided the proviso that the host cell is not a legionaminic acid naturally-producing cell, such as *Legionella pneumophilia, Campylobacter jejuni, Campylobacter coli* or *Clostridium botulinum*. However, as will be appreciated by one of skill in the art, as a result of the methods described herein, recombinant host cells of these organisms in which one or more of the enzymes listed above is over-produced, that is, synthesized or expressed at a greater level than in a comparable wild type cell may be engineered within the scope of the invention.

As many bacterial carbohydrate biosynthetic pathways, including hexosamine metabolism, proceed from fructose-6-phosphate, the above-described biosynthetic genes or synthesis methods may be used for the engineering of GDP-2,4-diacetamido-2,4,6-trideoxy-α-D-Glc (VIII), legionaminic acid (X) or CMP-legionaminic acid (XI) producing recombinant cells, for example, *Escherichia coil* cells although as will be appreciated by one of skill in the art other suitable organisms may be used as well as discussed above. Since we have described the genes necessary for the conversion of fructose-6-phosphate to VIII, X or XI, industrial suitable feedstocks such as glucose, fructose, glycerol, maltose or N-acetyl-glucosamine may be used for this E. coil in vivo production. Engineered E. coil cells may be similar to those of Lundgren and Boddy (2007), however cells would incorporate our genes for the production of I-VIII, I-X or I-XI.

Figure 2:
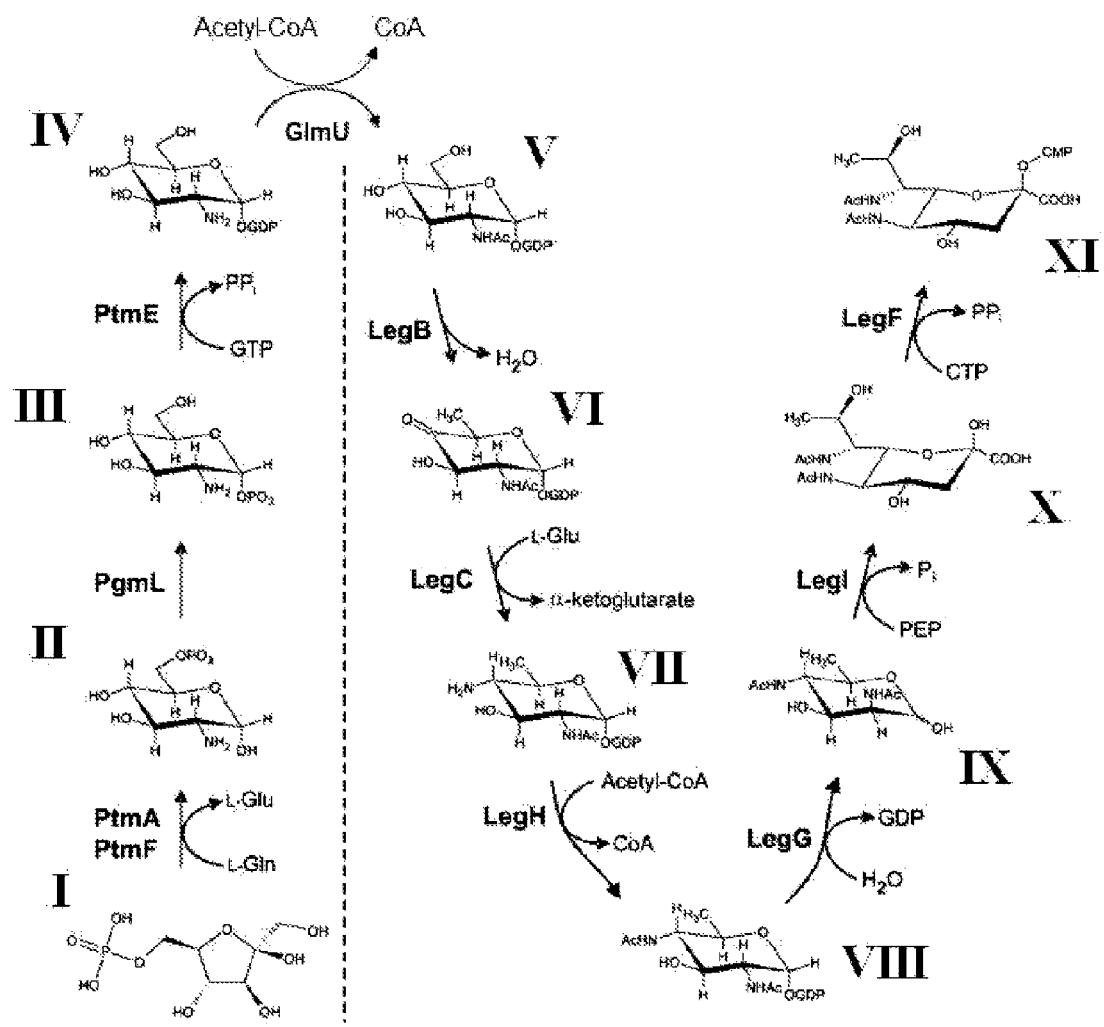
FIG. 2. The CMP-legionaminic acid biosynthetic pathway in *C. jejuni*. This biosynthetic pathway involves two segments: 1) synthesis of a GDP-sugar building block (left of the dashed line), and 2) synthesis of the final CMP-nonulosonate (right of the dashed line), which are linked by the enzymatic step shown in grey. The enzymes and biosynthetic intermediates of the CMP-legionaminic acid pathway in order are: PtmA and PtmF, glutaminase and isomerase, respectively, comprising a GlcN-6-P synthase; PgmL, phosphoglucosamine mutase; PtmE, GlcN-1-P guanylyltransferase; GlmU, N-acetyltransferase; LegB, NAD-dependent 4,6-dehydratase; LegC, PLP-dependent aminotransferase; LegH, N-acetyltransferase; LegG, NDP-sugar hydrolase/2-epimerase; LegI, legionaminic acid synthase; LegF, CMP-legionaminic acid synthetase; and (I) Fru-6-P; (II) GlcN-6-P; (III) GlcN-1-P; (IV) GDP-GlcN; (V) GDP-GlcNAc; (VI) GDP-2-acetamido-2,6-dideoxy-α-D-xylo-hexos-4-ulose; (VII) GDP-4-amino-4,6-dideoxy-α-D-GlcNAc; (VIII) GDP-2,4-diacetamido-2,4,6-trideoxy-α-D-glucopyranose; (IX) 2,4-diacetamido-2,4,6-trideoxy-D-mannopyranose; (X) legionaminic acid; (XI) CMP-legionaminic acid. The assignment of numbers to each compound is consistent with label designations found throughout the text. For simplicity, all the sugars are shown in $^4C_1$ form, except for the nonulosonates and Fru-6-P.

The sialic acid-like sugar legionaminic acid is found as a virulence-associated surface glycoconjugate in *Legionella pneumophila* and *Campylobacter coli*. In this work, we have purified and biochemically characterized eleven candidate biosynthetic enzymes from *C. jejuni*, thereby fully reconstituting the biosynthesis of legionaminic acid (X) and its CMP-activated form (XI), starting from fructose-6-P (I). This pathway involves unique GDP-linked intermediates and provides a facile means for the efficient large-scale synthesis of an important sialic acid mimic (FIG. 2; Tables 1 and 2).

Figure 3:
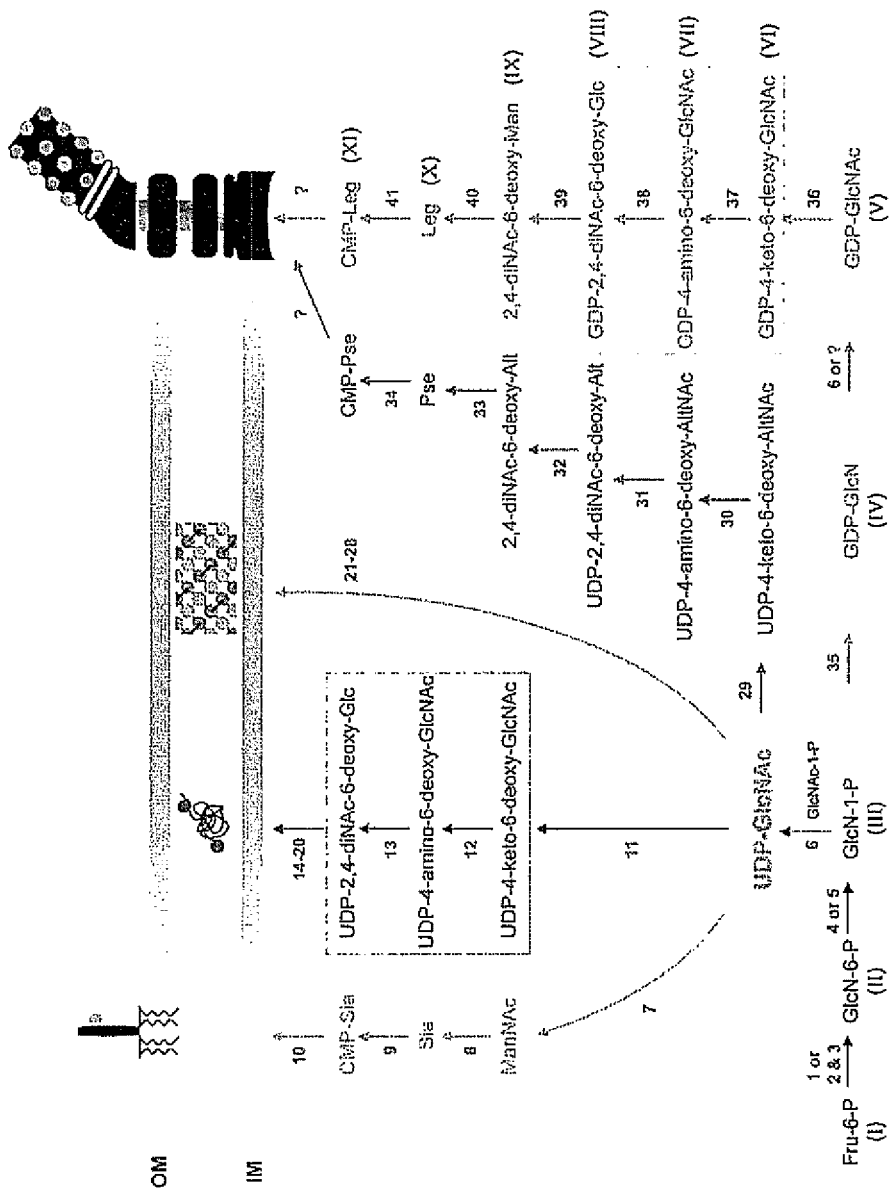
FIG. 3. A selection of extracytoplasmic sugar modifications from the *Campylobacter* cell. Glycosylated structures represented are lipooligosaccharide (cyan), periplasmic N-linked glycoproteins (purple), peptidoglycan (orange and blue) and flagella—a polymer of O-linked flagellin glycoproteins (green and red). Sugars found within boxes differ only by their nucleotide adduct, a likely discriminatory tool for these glycosylation pathways. To note, glycosyltransferases responsible for O-glycan attachment to flagellin have yet to be identified. Roman numeral designations are consistent with those found throughout the text, and refer to the CMP-legionaminic acid intermediates identified in this study. The enzymes (grey numbers) and alternate sugar names are found in Tables 3 and 4, respectively.
Figure 4:
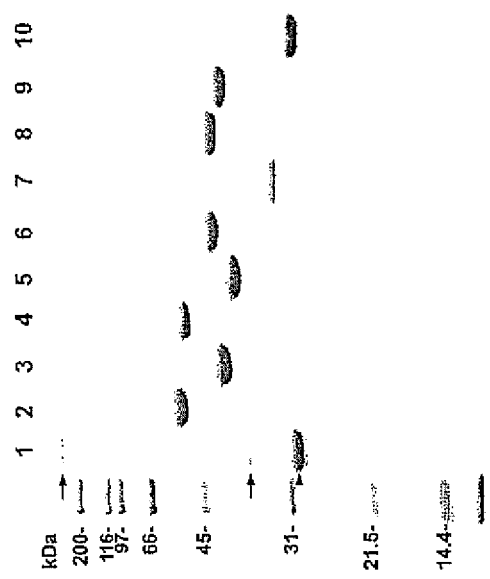
FIG. 4. Sodium dodecyl sulfate-polyacrylamide gel electrophoresis (12.5%) analyses of CMP-legionaminic acid biosynthetic enzymes from *Campylobacter jejuni* 11168 after nickel-nitrilotriacetic acid purification. Lane 1, PtmAHis$_6$ (arrowhead) and His$_6$PtmF (arrow); lane 2, PgmLHis$_6$; lane 3, His$_6$PtmE; lane 4, His$_6$GlmU; lane 5, LegBHis$_6$; lane 6, His$_6$LegC; lane 7, His$_6$LegH; lane 8, His$_6$LegG; lane 9, His$_6$LegI; lane 10, LegFHis$_6$. Molecular mass standards are shown on the left in kDa.

The elucidation of the legionaminic acid pathway within Campylobacter relied heavily on a 'holistic' approach involving bioinformatic, comparative genomic, metabolomic and functional analyses. One of the most significant insights was the consideration that this pathway may involve alternative nucleotide-linked intermediates. As it is well documented that different nucleotides within NDP-sugars allow for the separation of biosynthetic pathways, and importantly provides a means for their independent control and regulation, it was believed that the legionaminic acid pathway within Campylobacter may be selective for NDPs other than UDP. This would facilitate its separation from similar co-existing UDP-utilizing Campylobacter pathways, such as those for pseudaminic acid and 2,4-diacetamido-bacillosamine (FIG. 3). Several initial findings supported this hypothesis and are as follows. First, Cj1329, a member of the Campylobacter flagellin glycosylation locus (Cj1293-Cj1344), was found to exhibit sequence similarity to NDP-sugar pyrophosphorylases or nucleotidyltransferases, and in particular, possesses motifs similar to the characteristic activator (G-X-G-T-R-X2-P-X-T) [SEQ ID NO: 29]and sugar (E-E-K-P) [SEQ ID NO: 30]binding domains found within NDP-glucose pyrophosphorylases (Silva et al., 2005). In addition to the expected pathway components Cj1328, Cj1327 and Cj1331 (NeuC, B and A homologs), the gene products Cj1329, Cj1330 and Cj1332 were also found to be necessary for the accumulation of CMP-legionaminic acid (XI) in the metabolome of C. coil (McNally et al., 2007). The requirement of a possible nucleotidyltransferase supported our hypothesis and suggested that some members of the Cj1293-Cj1344 locus may be responsible for the production of a sugar-1-P precursor. Upon closer examination, Cj1332 and Cj1330 were found to share very limited sequence similarity with the N-terminal glutaminase and C-terminal amidation/isomerase domains, respectively, of glucosamine-6-P synthase, a key enzyme of hexosamine metabolism (Mouilleron et al., 2006). This was very surprising as glucosamine-6-P synthase contains both of these domains within one polypeptide, and the Cj1330/Cj1332 enzymes would be the first report where these domains are naturally being produced as two separate polypeptides. Our hypothesis was further supported by the very limited biosynthetic yields of XI obtained when using the Campylobacter NeuC, B and A homologs (Cj1328, Cj1327 and Cj1331) with Pgl enzyme-derived UDP-linked intermediates (FIG. 3). Interestingly, Glaze et al. (2008) recently reported similar difficulties, i.e. poor yields of XI, when using the same Pgl enzyme-derived UDP-linked intermediates with NeuC, B and A homologs from *L. pneumophila*. The remainder of this document will discuss our findings from in vitro functional analyses of eleven recombinantly produced and affinity purified enzymes from *C. jejuni* 11168 (FIG. 4). For the corresponding nomenclature and enzyme function associated with particular Cj numbers, please refer to Table 2 & FIGS. 12-21.

GDP-Glucosamine Biosynthesis.

Figure 12:
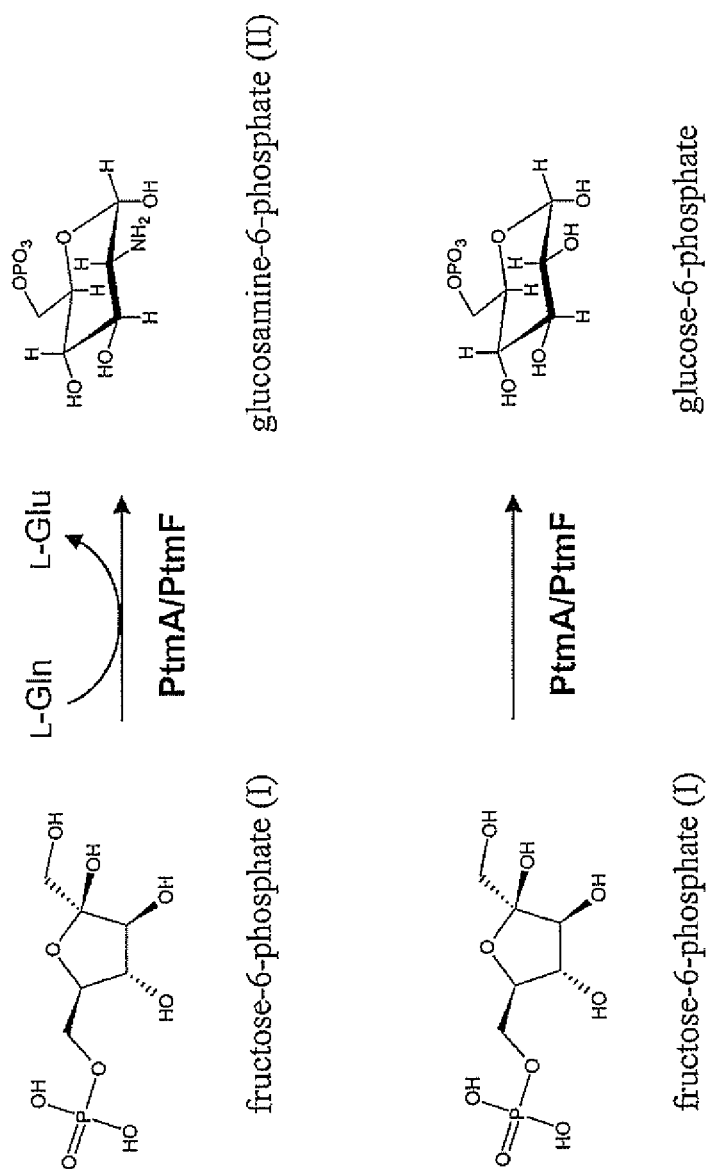
FIG. 12. The reactions catalyzed by PtmA and PtmF. PtmF is an isomerase that will convert fructose-6-phosphate (I) to glucose-6-phosphate. PtmF in combination with the glutaminase PtmA, and in the presence of L-glutamine, will also perform an amidation reaction resulting in the conversion of fructose-6-phosphate (I) to glucosamine-6-phosphate (II). Although these enzymatic reactions are not novel, the fact that these two enzymatic domains are naturally produced as two separate polypeptides, PtmF and PtmA, is unique.

Further evidence that Cj1330 (PtmF) and Cj1332 (PtmA) function in tandem as a glucosamine-6-P synthase (GlcN-6-P synthase), was the observed stabilization of PtmF by co-purification with PtmA. Attempts to isolate only PtmF resulted in aggregates that were unable to enter 12.5% SDS-polyacrylamide gels. When PtmF and PtmA were co-purified, the PtmF peptide still appeared to aggregate, as indicated by the presence of an additional higher molecular weight species by SDS-PAGE (FIG. 4), although to a much lesser extent. As observed for other GlcN-6-P synthases (Teplyakov et al., 1999), PtmF and PtmA were found to efficiently convert fructose-6-P (I) to glucosamine-6-P (II) or glucose-6-P depending on the presence or absence of L-glutamine, respectively (FIG. 12). To our knowledge, this is the first report of a GlcN-6-P synthase whose functional domains, glutaminase and isomerase, are not naturally fused, the significance of which is currently unknown.

Figure 13:
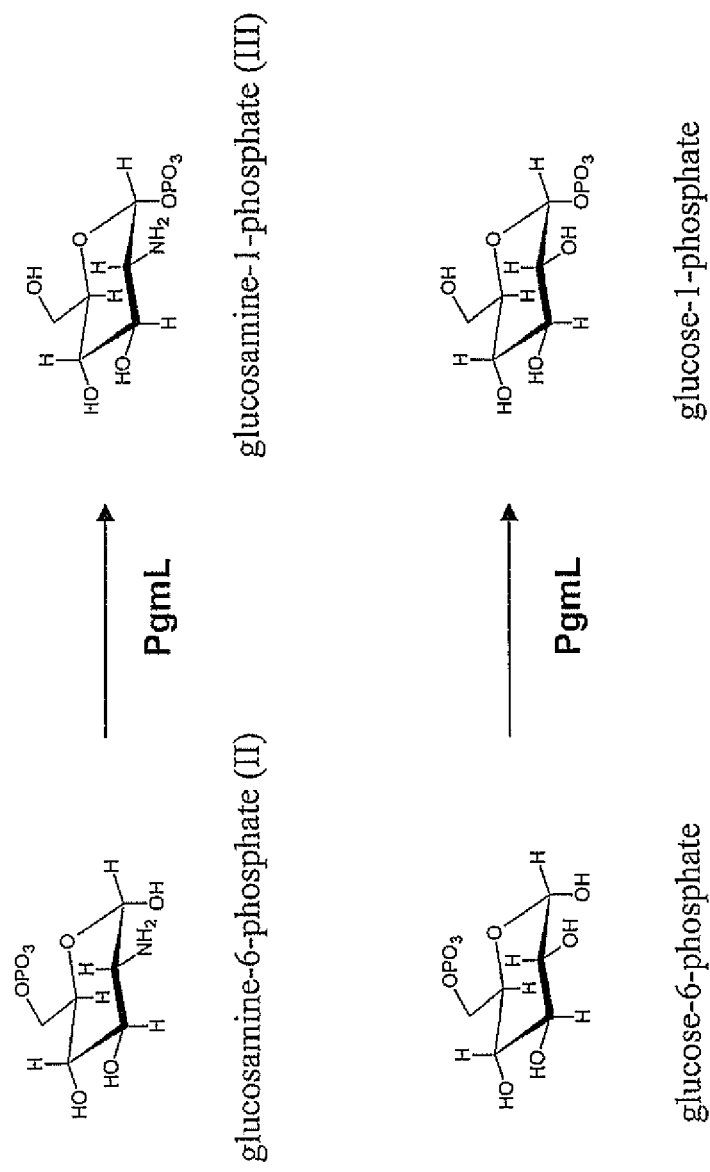
FIG. 13. The reactions catalyzed by PgmL. PgmL is a phosphoglucosamine mutase that will convert glucosamine-6-phosphate (II) to glucosamine-1-phosphate (III), as well as glucose-6-phosphate to glucose-1-phosphate, without exogenous addition of glucose-1,6-diphosphate or glucosamine-1,6-diphosphate that is typically required for other phosphoglucosamine mutase enzymes. PgmL along with PtmF, PtmA and PtmE allowed for a one-pot synthesis of GDP-glucosamine (IV) from fructose-6-phosphate (I), an important function for in vivo production.

The next committed step in bacterial hexosamine biosynthesis would involve conversion of II to glucosamine-1-P (III) by a phosphoglucosamine mutase. The appropriate mutase was unclear, and as such, we had to look outside of the flagellar glycosylation locus. As the GlcN-6-P synthase is the rate-limiting enzyme in hexosamine metabolism, it was believed that a general 'house-keeping' mutase might be sufficient enough to perform the necessary interconversions for flagellin glycosylation. Originally, Cj0360 or GlmM, an annotated mutase protein, was tested. Although, it only appeared to accumulate GlcN-1,6-diP from II. Surprisingly, the gene Cj1407c was also annotated as a phosphoglucomutase, which just so happens to be juxtaposed to fliL (Cj1408), a flagellar component that localizes to the cytoplasmic face of the flagellar basal body MS ring in Campylobacter. Cj1407c, now annotated as PgmL for its involvement in the legionaminic acid pathway, catalyzed the interconversion of II to III (FIG. 13) without exogenous addition of Glc-1,6-diP or GlcN-1,6-diP that is typically required for GlmM enzymes (Mengin-Lecreulx and van Heijenoort, 1996; Jolly et al., 1999), and allowed for a 'one-pot' enzymatic synthesis of GDP-GlcN (IV) (see below). Cj1407c or PgmL was also capable of converting Glc-6-P o Glc-1-P (FIG. 13).

Figure 9:
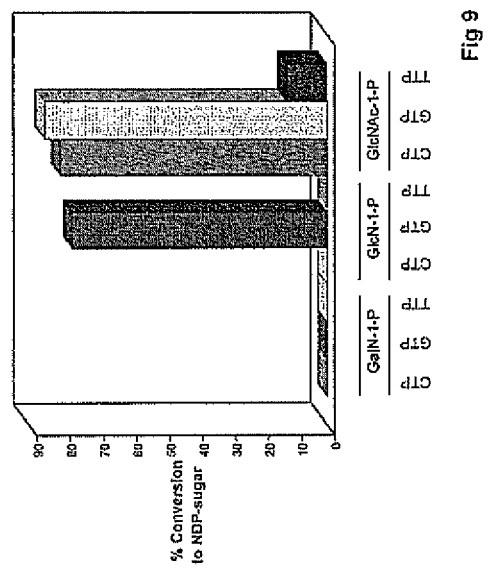
FIG. 9. Substrate flexibility of His$_6$PtmE after a 30 min incubation at 37° C.
Figure 14:
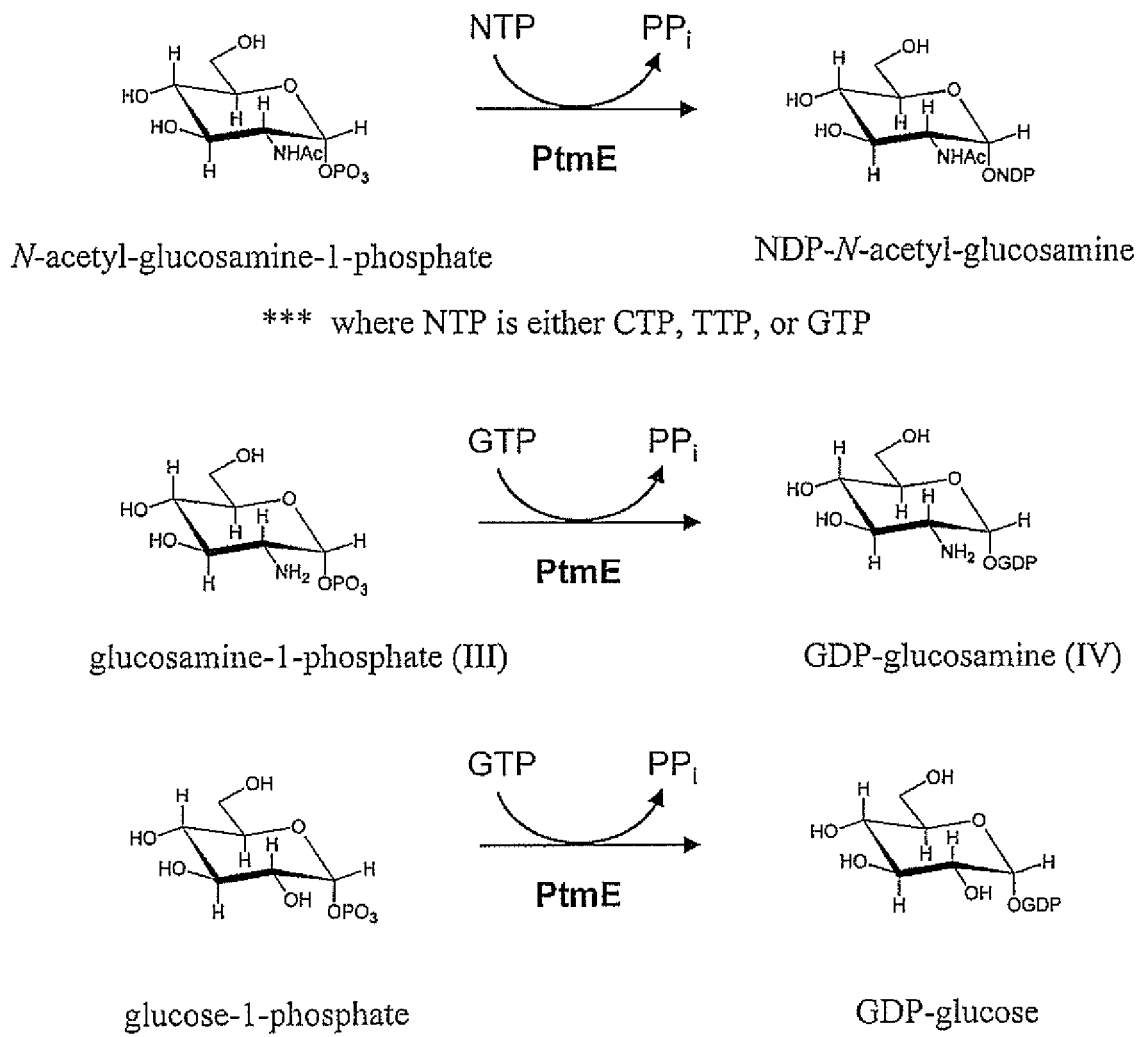
FIG. 14. The reactions catalyzed by PtmE. PtmE is an NDP-sugar pyrophosphorylase or nucleotidyltransferase that will convert N-acetyl-glucosamine-1-phosphate to CDP-N-acetyl-glucosamine, GDP-N-acetyl-glucosamine (V) and TDP-N-acetyl-glucosamine using the nucleotides CTP, GTP and TTP, respectively. It will also convert glucose-1-phosphate to GDP-glucose using the nucleotide GTP. Finally, when using a glucosamine-1-phosphate sugar acceptor, it is specific for GTP, forming GDP-glucosamine (IV). It is this latter function that is likely to be its role in vivo, and thus this enzyme may be referred to as a glucosamine-1-phosphate guanylyltransferase. To the best of our knowledge, the specific and efficient glucosamine-1-phosphate guanylyltransferase function is novel.

In determining the nucleotide utilized by the legionaminic acid pathway, we initially looked at the specificity of the nucleotidyltransferase. Cj1329, or PtmE, was found to be absolutely specific for GTP in reactions involving III (FIGS. 9 and 14). Importantly, this enabled the large-scale production and purification of GDP-GlcN (IV) (FIG. 5a and Table 5). In addition, when using GlcNAc-1-P as a sugar acceptor, PtmE exhibited promiscuity with respect to activator NTP donors (FIGS. 9 and 14). This allowed for the large-scale production and purification of GDP-GlcNAc (V), CDP-GlcNAc and TDP-GlcNAc (Tables 1 and 5) for further testing within the pathway. As eukaryotes accumulate GlcNAc-1-P primarily due to the actions of a glucosamine-6-P N-acetyltransferase (Buse et al., 1996), we were surprised at the NTP donor promiscuity of PtmE with a GlcNAc-1-P sugar acceptor. However, we surmised that possibly bacterial cells accumulate GlcN-1-P instead of GlcNAc-1-P due to the bifunctional nature of the UDP-GlcNAc forming enzyme GlmU (Mengin-Lecreulx and van Heijenoort, 1994), and that maybe the natural function of PtmE within the legionaminic acid pathway is the formation of GDP-GlcN (IV) from GlcN-1-P (III). If this scenario is correct, then the legionaminic acid pathway would be expected to utilize guanine nucleotide precursors. Ultimately, this was confirmed upon further testing of pathway components (see below). In addition, PtmE exhibited specificity for the C4 configuration of Glc as no activity was observed when using GalN-1-P (FIG. 9), but activity was observed with Glc-1-P, GlcN-1-P and GlcNAc-1-P (FIG. 14). To note, ptmE contains additional upstream sequence of unknown function called a CBS domain (originally found in cystathione beta-synthase), which may be involved at some level of regulation.

Figure 5:
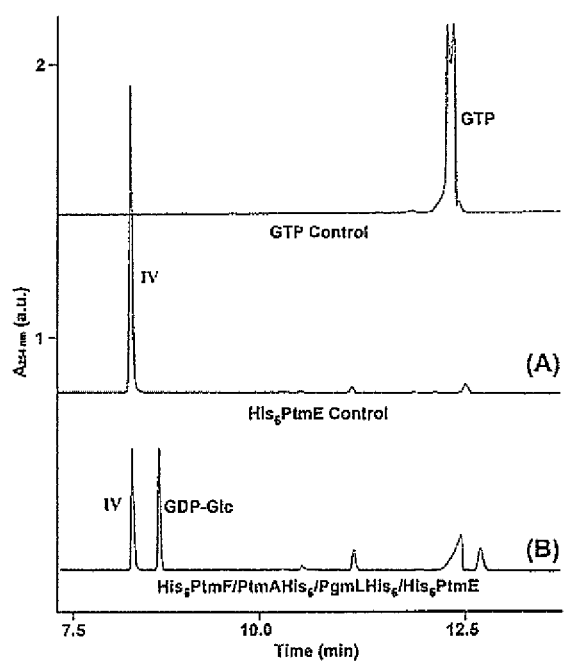
FIG. 5. Capillary electrophoresis analysis of a 'one-pot' enzymatic reaction forming GDP-GlcN from Fru-6-P. A control PtmE reaction (A) initially contained GlcN-1-P (III), GTP, and His$_6$PtmE, while the 'one-pot' reaction (B) contained Fru-6-P (I), GTP and each of His$_6$PtmF, PtmAHis$_6$, PgmLHis$_6$ and His$_6$PtmE. The locations of GTP, IV and GDP-α-D-Glc are also indicated within the figure. a.u., arbitrary units.

The efficiency of these NDP-hexosamine enzymes was demonstrated by the production of IV from a 'one-pot' enzymatic reaction involving PtmF, PtmA, PgmL and PtmE, starting from 1 (FIG. 5). In addition to IV, the accumulation of GDP-Glc was also observed in the 'one-pot' reaction, a consequence of PtmF/PtmA producing Glc-6-P upon depletion of L-glutamine as well as promiscuity of downstream enzymes. The identities of the two products observed in FIG. 5b were confirmed by further purification and CE-MS analyses, NMR analyses (Table 5), and comparisons with a control preparation of IV (FIG. 5a).

Conversion of GDP-GlcN to GDP-GlcNAc.

Figure 10:
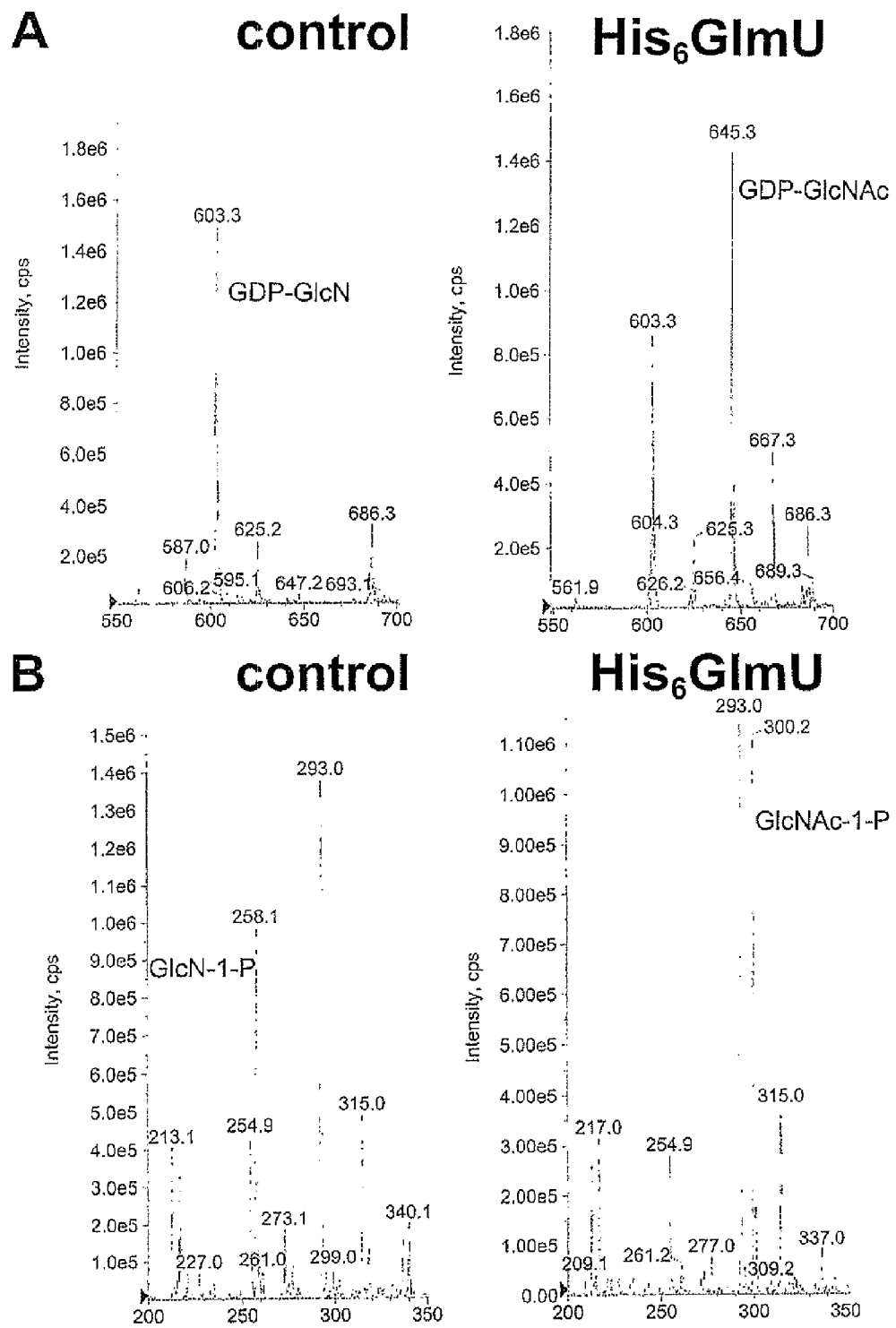
FIG. 10. CE-MS analysis (negative ion mode) of the His$_6$GlmU reaction. (A) Conversion of GDP-GlcN (IV) to GDP-GlcNAc (V). The reaction initially contained GDP-GlcN, acetyl-CoA, and His$_6$GlmU. (B) Conversion of GlcN-1-P (III) to GlcNAc-1-P. The reaction was performed similar to above, except that III was included instead of IV.
Figure 15:
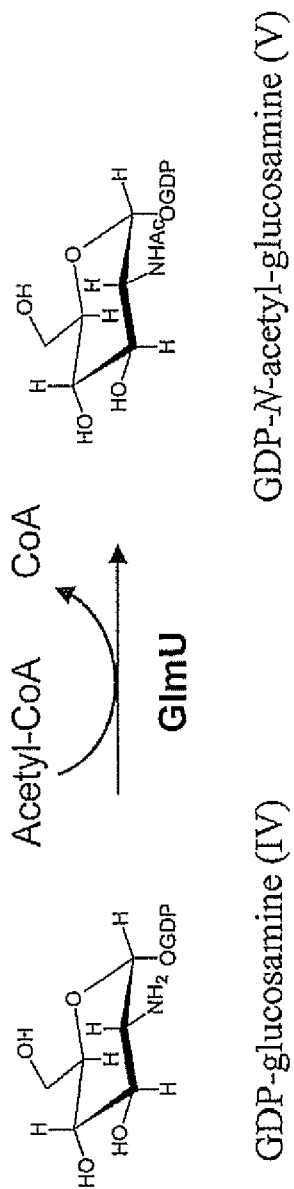
FIG. 15. The reaction catalyzed by GlmU. GlmU is bifunctional, being an N-acetyl-glucosamine-1-phosphate uridyltransferase and glucosamine-1-phosphate (III) N-acetyltransferase. It is a well-established enzyme converting glucosamine-1-phosphate (III) to UDP-N-acetyl-glucosamine in two steps. We report for the first time that GlmU may also convert GDP-glucosamine (IV) to GDP-N-acetyl-glucosamine (V) by catalyzing N-acetyl transfer from acetyl-CoA.

As the synthesis of legionaminic acid (X) would be expected to utilize a 2,4-diacetamido-hexose sugar, the assumption was that a GDP-HexNAc intermediate fed into the nonulosonate pathway, thereby reducing the number of enzymatic manipulations required, i.e IV wasn't the initial nonulosonate building block. This was later confirmed, as the initial nonulosonate pathway enzyme exhibited preference for the N-acetyl group of V (see below). Of all the enzymatic manipulations leading to the nonulosonate pathway precursor V, it is this step in which we are most uncertain. Since the bifunctional UDP-GlcNAc forming enzyme GlmU, which is responsible for the conversion of III to GlcNAc-1-P with subsequent uridylation, is capable of converting UDP-GlcN to UDP-GlcNAc at low efficiencies (Pompeo et al., 2001), we sought to determine if Campylobacter GlmU was able to N-acetylate IV. This GlmU was found to convert IV to V, but not to completion as is seen with a control N-acetylation reaction using its natural substrate III instead of IV (FIGS. 10 and 15). We are currently screening other putative N-acetyltransferases from the flagellar glycosylation locus, such as Cj1296/97, Cj1321 and Cj1322/23, for their ability to catalyze efficient conversion of IV to V. Finally, we don't believe the pathway would initially proceed I→II→III→GlcNAc-1-P→V, as the promiscuous nature of PtmE with GlcNAc-1-P would likely result in lowered synthesis of V, but we cannot rule out this possibility. Importantly, our suggested scheme (FIG. 2) would also allow PtmE to act on abundant levels of endogenous III.

Biosynthesis of CMP-Legionaminic Acid from GDP-GlcNAc.

Figure 6:
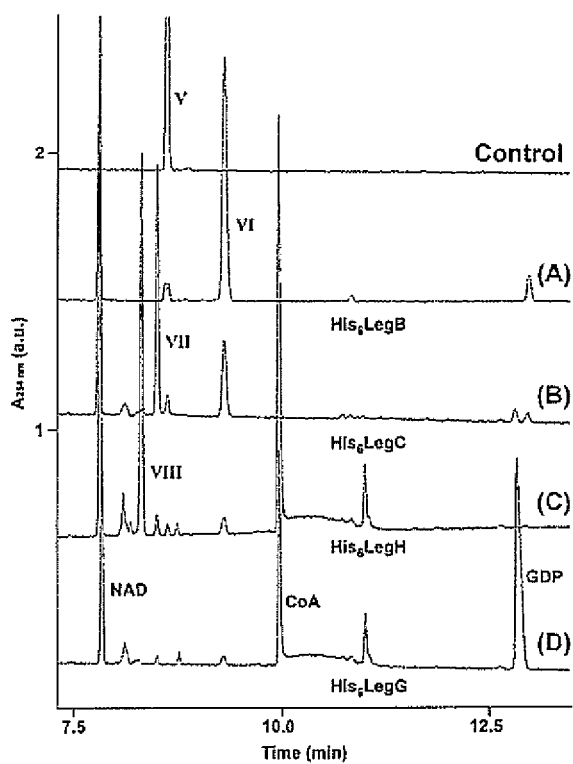
FIG. 6. Capillary electrophoresis analysis of the reaction products obtained after the sequential addition of LegBHis$_6$ (A), His$_6$LegC (B), His$_6$LegH (C), His$_6$LegG (D) to GDP-α-D-GlcNAc. Reactions contained 1 mM GDP-α-D-GlcNAc, 0.5 mM NAD, 0.8 mM PLP, 8 mM L-Glu, and 1.5 mM acetyl-CoA as required. The locations of GDP-α-D-GlcNAc (V), GDP-2-acetamido-2,6-dideoxy-α-D-xylo-hexos-4-ulose (VI), GDP-4-amino-4,6-dideoxy-α-D-GlcNAc (VII), GDP-2,4-diacetamido-2,4,6-trideoxy-α-D-Glc (VIII), NAD, CoA and GDP are indicated within the figure. a.u., arbitrary units.
Figure 16:
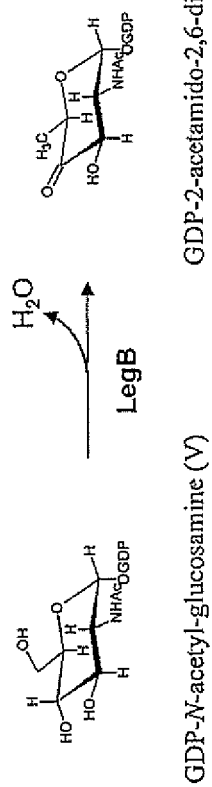
FIG. 16. The reaction catalyzed by LegB. LegB is an NAD$^+$-dependent GDP-N-acetyl-glucosamine 4,6-dehydratase that will convert GDP-N-acetyl-glucosamine (V) to GDP-2-acetamido-2,6-dideoxy-α-D-xylo-hexos-4-ulose (VI). To the best of our knowledge, both the activity and product of LegB is novel.

Using the knowledge gained from elucidating the CMP-pseudaminic acid pathway in *Helicobacter pylori* (Schoenhofen, Lunin et al., 2006; Schoenhofen, McNally, Brisson et al., 2006; Schoenhofen, McNally, Vinogradov et al., 2006), we began unraveling the biosynthetic route for XI, the findings of which are summarized in FIG. 2 and Table 1. Recent metabolomics findings discounted Cj1319 (LegB) and Cj1320 (LegC), the only remaining putative dehydratase and aminotransferase left in the Campylobacter flagellar glycosylation locus, as having a role in legionaminic acid synthesis (McNally et al., 2007), although we found these enzymatic manipulations necessary within the pathway. By examining the ability of LegB to act as a dehydratase, we found it to perform C4,6 dehydration of V (FIG. 16). Initially reactions only included V and LegB, but failed. As NAD(P)$^+$ is usually tightly coupled to these particular enzymes and is a necessary cofactor for the C4,6 dehydratase reaction, we added NAD$^+$ and NADP$^+$ exogenously in separate reactions. In doing so, LegB was found to catalyze the efficient turnover of V in an NAD$^+$-dependent manner forming the product GDP-2-acetamido-2,6-dideoxy-α-D-xylo-hexos-4-ulose (VI; FIGS. 6a and 16). To note, other LegB reactions, in the presence or absence of NAD(P)$^+$, with IV, UDP-GlcNAc, CDP-GlcNAc, TDP-GlcNAc and TDP-Glc did not yield discernable product.

Figure 17:
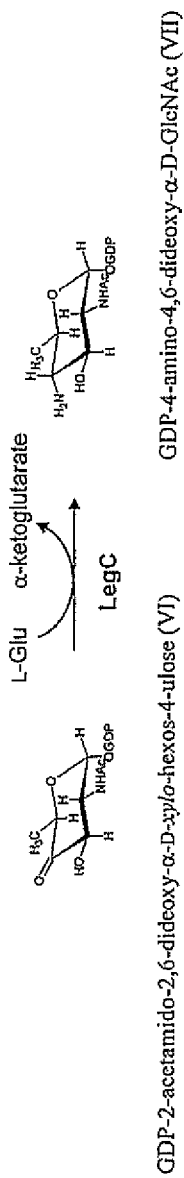
FIG. 17. The reaction catalyzed by LegC. LegC is a PLP-dependent GDP-2-acetamido-2,6-dideoxy-α-D-xylo-hexos-4-ulose aminotransferase that will convert GDP-2-acetamido-2,6-dideoxy-α-D-xylo-hexos-4-ulose (VI) to GDP-4-amino-4,6-dideoxy-α-D-GlcNAc (VII) in the presence of PLP and L-glutamate. To the best of our knowledge, the activity, substrate and product of LegC are novel.

Furthermore, LegC catalyzed the efficient aminotransfer of VI, forming GDP-4-amino-4,6-dideoxy-α-D-GlcNAc (VII) in a PLP-dependent manner (FIGS. 6b and 17). LegC is specific for the GDP-keto intermediate VI, as it was unable to convert the UDP-keto intermediates from the pseudaminic acid or 2,4-diacetamido-bacillosamine pathways (FIG. 3), further support for its role in legionaminic acid synthesis. The in vivo metabolomic and in vitro enzymatic discrepancy for LegB/LegC may be explained by possible low-level crosstalk of pathway intermediates within Campylobacter. This is further strengthened by our observation that low-levels of XI may be obtained from using UDP-linked intermediates from the Pgl 2,4-diacetamido-bacillosamine pathway.

Figure 18:
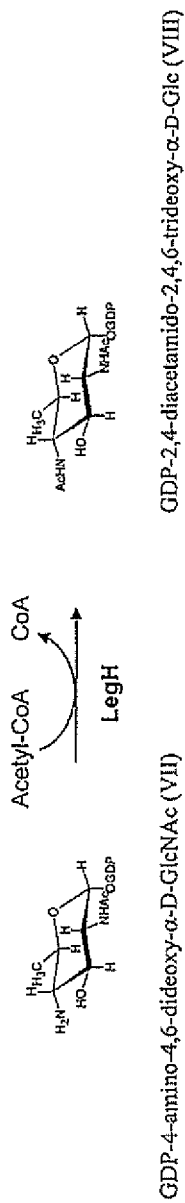
FIG. 18. The reaction catalyzed by LegH. LegH is a GDP-4-amino-4,6-dideoxy-α-D-GlcNAc N-acetyl-transferase that will convert GDP-4-amino-4,6-dideoxy-α-D-GlcNAc (VII) to GDP-2,4-diacetamido-2,4,6-trideoxy-α-D-Glc (VIII) in the presence of acetyl-CoA. To the best of our knowledge, the activity, substrate and product of LegH are novel.

The next expected step in the synthesis of XI would involve N-acetylation of VII by a respective transferase. As there are several such uncharacterized transferases in the Campylobacter flagellin glycosylation locus (Cj1296/97, Cj1298, Cj1321, and Cj1322/23), we initially attempted reactions with PglD, an N-acetyltransferase involved in Pgl 2,4-diacetamido-bacillosamine (FIG. 3) biosynthesis (Olivier et al., 2006). The normal substrate of PglD is identical to VII only it is UDP-linked. To our surprise, PglD was able to catalyze N-acetyltransfer of VII, forming GDP-2,4-diacetamido-2,4,6-trideoxy-α-D-Glc (VIII). Although, the eventual screening of Cj1298 (LegH) exhibited much greater catalytic rates, resulting in 100% conversion of VII to VIII (FIGS. 6c and 18). As such, LegH is likely a dedicated component of legionaminic acid biosynthesis. Importantly, this in vitro cross-complementation of LegH function by PglD may have prevented its initial identification by in vivo metabolomics screening. Importantly, without our in vitro identification of LegB, LegC and LegH, the efficient enzymatic production of VIII and subsequent intermediates/products would not be possible.

Figure 7:
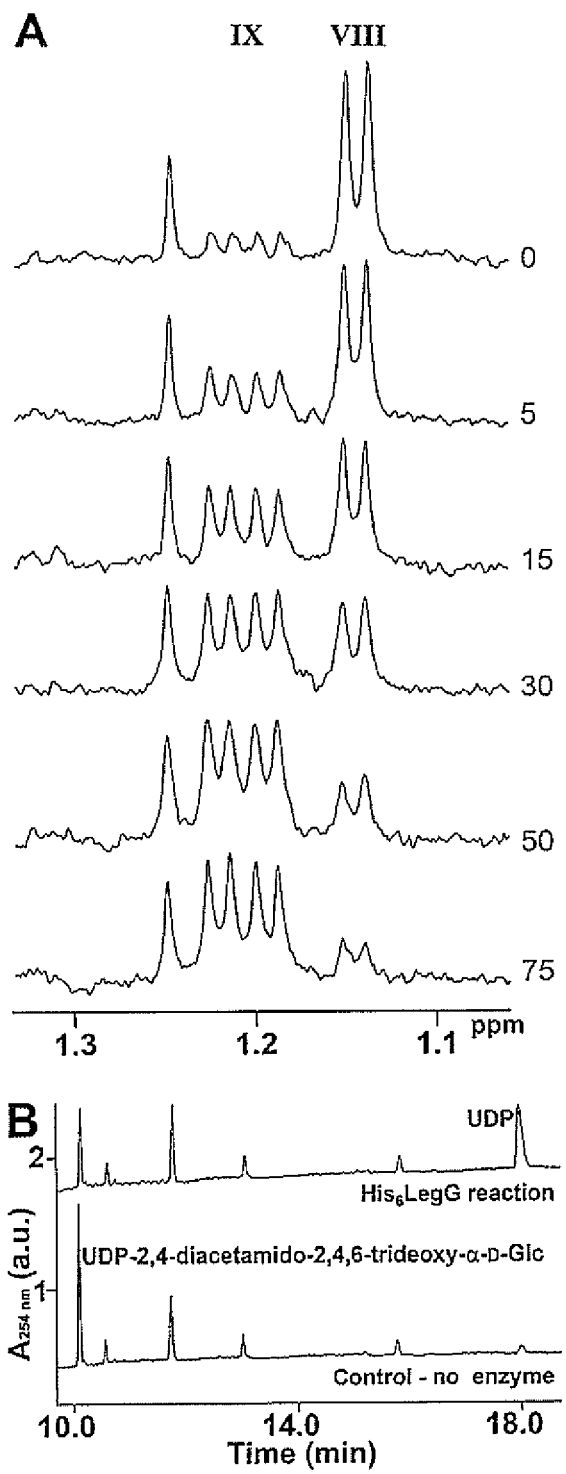
FIG. 7. Kinetics and substrate specificity of His$_6$LegG. (A) The His$_6$LegG reaction with GDP-2,4-diacetamido-2,4,6-trideoxy-α-D-Glc (VIII) monitored directly with $^1$H NMR spectroscopy. $^1$H NMR spectra were acquired over time (min) as indicated, and the C-6CH$_3$ proton region of substrate (VIII) and product (IX) is shown. (B) Capillary electrophoresis analysis of the His$_6$LegG reaction with UDP-2,4-diacetamido-2,4,6-trideoxy-α-D-Glc after incubation for 90 min at 37° C. and then 16 h at 25° C., using ~10-fold more enzyme than in A. The locations of UDP and UDP-2,4-diacetamido-2,4,6-trideoxy-α-D-Glc are indicated within the figure, where a.u. is arbitrary units.
Figure 11:
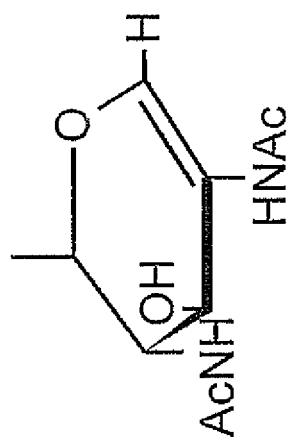
FIG. 11. The product formed from His$_6$LegG catalysis of UDP-2,4-diacetamido-2,4,6-trideoxy-α-D-Glc. From preliminary $^1$H and $^{13}$C NMR data, the product appears to be 6-deoxy-2,4-diacetamidoglucal.
Figure 19:
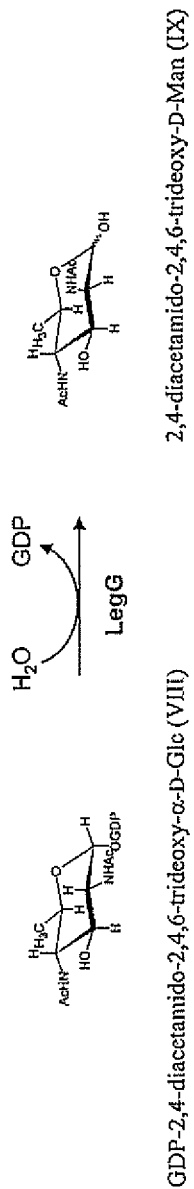
FIG. 19. The reaction catalyzed by LegG. LegG is a hydrolysing GDP-2,4-diacetamido-2,4,6-trideoxy-α-D-Glc 2-epimerase that will convert GDP-2,4-diacetamido-2,4,6-trideoxy-α-D-Glc (VIII) to 2,4-diacetamido-2,4,6-trideoxy-D-Man (IX). To the best of our knowledge, the specific activity and substrate of LegG is novel.

Likely the most critical checkpoint between the Pgl glycan and legionaminic acid pathways within Campylobacter is the reaction catalyzed by the NeuC homolog Cj1328 (LegG). This enzyme is expected to perform a C2 epimerization resulting in NDP removal, and in fact, LegG was found to efficiently remove the NDP from substrate VIII (FIG. 6d). Upon examination of the sugar product formed, by performing 'in-tube' NMR reactions, we observed efficient catalysis of VIII, such that the formation of 2,4-diacetamido-2,4,6-trideoxy-D-Man (IX) was near completion within 75 min using only 4 µg of LegG (FIGS. 7a and 19). Using similar conditions, IX was not observed when the product of PglD, UDP-2,4-diacetamido-2,4,6-trideoxy-α-D-Glc, was used as a substrate. Although, when we increased the quantity of LegG 10-fold within this reaction, UDP removal was observed (FIG. 7b), but product IX was not. Instead, we observed small quantities of 6-deoxy-2,4-diacetamidoglucal (FIG. 11), an unlikely candidate for the next condensation reaction. As we were able to generate small quantities of XI using the UDP-linked intermediate above, similar to recent findings by Glaze et al. (2008), it is possible that the glucal product, or non-detectable quantities of IX, may inefficiently condense with pyruvate in the next enzymatic step. However, we conclude that the natural synthetic route is as summarized in FIG. 2. To note, LegG was also found to catalyze turnover of V with moderate efficiency as assessed by CE, which may be an alternative means of accumulating the sialic acid precursor ManNAc within Campylobacter. This is the reason our large-scale biosynthesis of X involved two separate 'one-pot' reactions (i.e. V→VIII then VIII→X).

Figure 20:
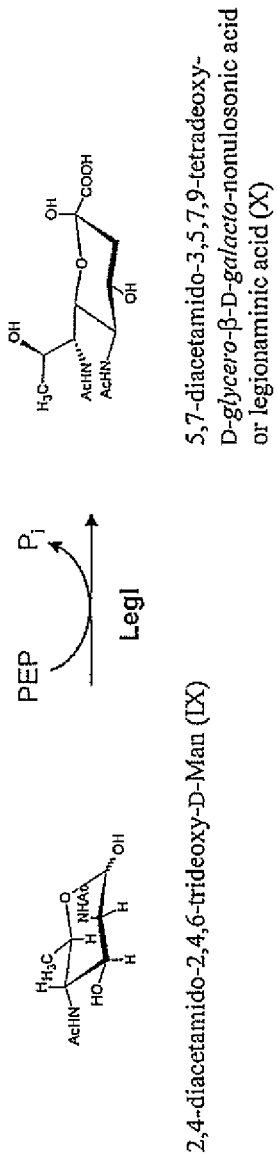
FIG. 20. The reaction catalyzed by LegI. LegI is a legionaminic acid synthase that will convert 2,4-diacetamido-2,4,6-trideoxy-D-Man (IX) to 5,7-diacetamido-3,5,7,9-tetradeoxy-D-glycero-D-galacto-nonulosonic acid or legionaminic acid (X) by condensing IX with pyruvate, using PEP and releasing inorganic phosphate. This enzyme provides a far superior production of X than that reported previously.
Figure 21:
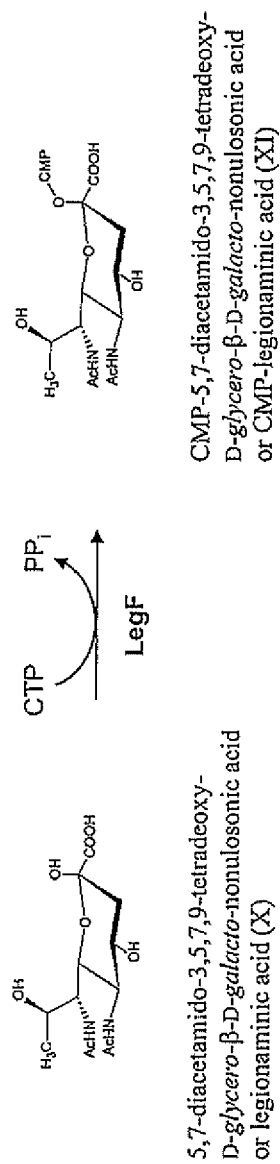
FIG. 21. The reaction catalyzed by LegF. LegF is a CMP-legionaminic acid synthetase that will convert 5,7-diacetamido-3,5,7,9-tetradeoxy-D-glycero-D-galacto-nonulosonic acid or legionaminic acid (X) to CMP-5,7-diacetamido-3,5,7,9-tetradeoxy-D-glycero-D-galacto-nonulosonic acid or CMP-legionaminic acid (XI) using the NTP donor CTP and releasing pyrophosphate.

Finally, the roles of the NeuB and NeuA homologs Cj1327 (LegI) and Cj1331 (LegF), respectively, were confirmed. LegI catalyzed the condensation of IX with pyruvate to form X, while LegF efficiently CMP-activated X (Table 1; FIGS. 20 and 21).

Figure 8:
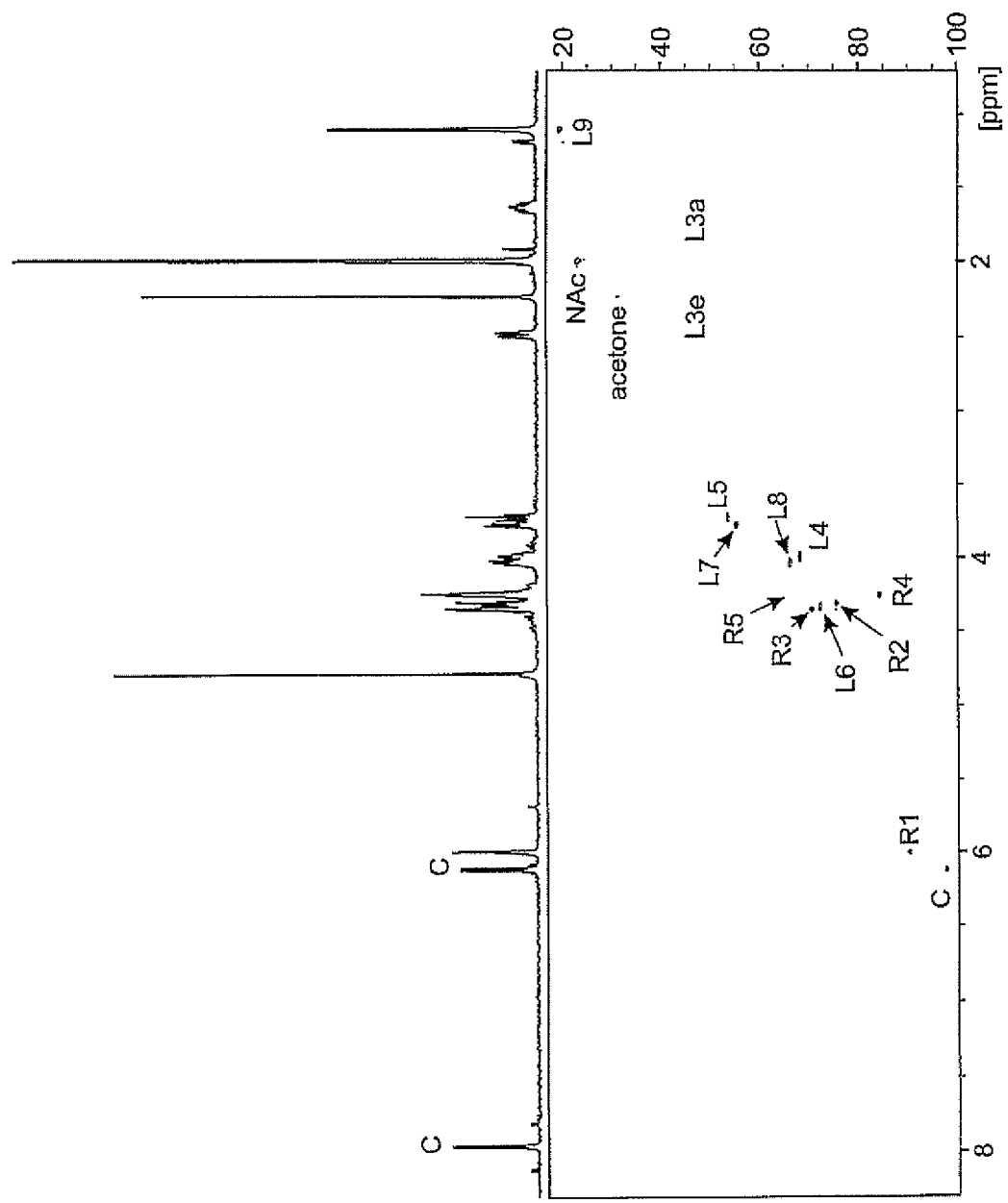
FIG. 8. $^1$H spectrum and $^1$H—$^{13}$C HSQC correlation spectrum of CMP-legionaminic acid (XI). Spectra were recorded on a Varian INOVA UNITY 500 MHz spectrometer with standard Varian pulse sequences in D$_2$O at 25° C., with 4 scans for $^1$H spectrum and 32 scans for HSQC. C, cytosine; R, ribose; L, legionaminic acid; NAc, 5-NHAc and 7-NHAc CH$_3$ regions of legionaminic acid; and acetone was included as an internal reference.

In summary, we have outlined a facile and efficient method for the enzymatic preparation of XI (FIG. 8), and the corresponding pathway intermediates. As synthetic yields obtained from chemical methods are low, only 7% from condensation of IX with oxaloacetic acid (Tsvetkov et al., 2001), our enzymatic method provides an attractive synthetic alternative. And, since we have defined the NDP-hexosamine enzymatic steps from I, the engineering of *E. coli* producing strains is now possible (Lundgren and Boddy, 2007), with production efficiencies far-surpassing those from in vitro enzymatic methods.

EXPERIMENTAL PROCEDURES

His$_6$-Tagged Protein Expression and Purification

Plasmid DNA construction and sequencing were similar to previously described methods (Schoenhofen et al., 2006a; Schoenhofen et al., 2006b). Vector or recombinant plasmids were transformed by electroporation into electrocompetent Top10F' or DH10B (Invitrogen) *Escherichia coil* cells for cloning purposes or BL21[DE3] (Novagen) *E. coli* cells for protein production, except for the expression clone pNRC51.1 which was electroporated into BL21-CodonPlus [DE3]-RIL (Novagen) *E. coil* cells. PCR was used to amplify *Campylobacter jejuni* 11168 DNA for subsequent cloning. A list of cloning vectors and recombinant plasmids is provided in Table 6, and pertinent oligonucleotides are provided in Table 7. Newly constructed plasmids are: pNRC145.3, encoding an N-terminal His$_6$-tagged derivative of Cj1330 or PtmF; pNRC141.1, encoding a C-terminal His$_6$-tagged derivative of Cj1332 or PtmA; pNRC173.1, encoding a C-terminal His$_6$-tagged derivative of Cj1407c or PgmL; pNRC136.1, encoding an N-terminal His$_6$-tagged derivative of Cj1329 or PtmE; pNRC175.1, encoding an N-terminal His$_6$-tagged derivative of Cj0821 or GlmU; pNRC16.1, encoding a C-terminal His$_6$-tagged derivative of Cj1319 or LegB; pNRC83.1, encoding an N-terminal His$_6$-tagged derivative of Cj1320 or LegC; pNRC164.3, encoding an N-terminal His$_6$-tagged derivative of Cj1298 or LegH; pNRC134.1, encoding an N-terminal His$_6$-tagged derivative of Cj1328 or LegG; pNRC51.1, encoding an N-terminal His$_6$-tagged derivative of Cj1327 or LegI; and pNRC139.1, encoding a C-terminal His$_6$-tagged derivative of Cj1331 or LegF.

Typically, each expression strain was grown in 1 to 2 l of 2× yeast tryptone (Schoenhofen et al., 2006a), depending on expression level, with either kanamycin (50 μg ml$^{-1}$), ampicillin (75 μg ml$^{-1}$) or ampicillin and chloramphenicol (100 μg ml$^{-1}$ and 40 μg ml$^{-1}$) for selection. The cultures were grown at 30° C., induced at an OD$_{600}$ of 0.6 with 0.1 mM isopropyl-1-thio-β-D-galactopyranoside, and harvested 2.75 h later. For the 'GDP-hexosamine' biosynthetic enzymes (PtmF, PtmA, PgmL, and PtmE), cell pellets were resuspended in lysis buffer (25 mM Tris, pH 7.5, 400 mM NaCl, 10 mM β-mercaptoethanol) containing 10 mM imidazole and complete protease inhibitor mixture, EDTA-free (Roche Applied Science). After addition of 10 μg ml$^{-1}$ of DNaseI (Roche Applied Science), the cells were disrupted by two passes through an emulsiflex C5 (20,000 psi). Lysates were centrifuged at 100,000×g for 50 min at 4° C., and the supernatant fraction was applied to a 2 ml nickel-nitrilotriacetic acid (Qiagen) column equilibrated in 10 mM imidazole lysis buffer, using a flow rate of 1 ml min$^{-1}$. After sample application, the column was washed with 10 column volumes of 10 mM imidazole lysis buffer. To elute the protein of interest, a linear gradient from 10 to 100 mM imidazole, in lysis buffer, over 25 column volumes was applied to the column prior to a final pulse of 20 column volumes of 200 mM imidazole lysis buffer. Fractions containing the purified protein of interest, as determined by SDS-PAGE (12.5%) and Coomassie staining, were pooled and dialyzed against dialysis buffer (25 mM Tris, pH 7.5) overnight at 4° C. When purifying PtmE for the 'large-scale' production of NDP-sugars, the dialysis buffer contained 50 mM Tris pH 7.5. In addition, PtmF and PtmA were purified together by combining respective resuspended cell pellets before cell lysis. For the 'nonulosonate' biosynthetic enzymes (LegB, LegC, LegH, LegG, LegI and LegF) and GlmU, purification was similar to that above, except that the lysis buffer contained 50 mM sodium phosphate instead of Tris and the dialysis buffer consisted of 25 mM sodium phosphate, 25 mM NaCl. The pH was adjusted from 7.3 to 7.8 depending on the theoretical pI of each protein. Furthermore, the dialysis buffer for GlmU additionally contained 10 mM β-mercaptoethanol. Protein concentration was measured spectrophotometrically using A$_{280}$ 0.1% values (PgmLHis$_6$, 0.693; His$_6$PtmE, 0.513; His$_6$GlmU, 0.517; LegBHis$_6$, 0.892; His$_6$LegC, 0.625; His$_6$LegH, 1.06; His$_6$LegG, 0.432; His$_6$LegI, 0.242; LegFHis$_6$, 0.385; and protein concentration was estimated for His$_6$PtmF/PtmAHis$_6$ preparations using an averaged 0.1% value of 0.82). Yields of purified protein were typically 20 mg l$^{-1}$ of cell culture, except for His$_6$LegC, His$_6$LegH and His$_6$LegI with yields of 6, 2.5, and 7.5 mg l$^{-1}$ of cell culture, respectively.

Enzymatic Reactions and Metabolite Purification

Enzymatic reactions were performed for 4.5 h at 37° C., and then overnight at 25° C., with approximately 200 μg ml$^{-1}$ respective protein concentration using chemicals from Sigma (unless otherwise indicated). GDP-glucosamine biosynthesis. The 'one-pot' enzymatic synthesis of GDP-GlcN from Fru-6-P (I→IV) was accomplished using a 3 ml reaction containing His$_6$PtmF, PtmAHis$_6$, PgmLHis$_6$, His$_6$PtmE, 5 mM Fru-6-P (I), 10 mM L-Gln, 1 mM DTT, 5 mM MgCl$_2$, 0.8 U ml$^{-1}$ pyrophosphatase, and 2.5 mM GTP in 25 mM Tris pH 7.5. Large-scale enzymatic synthesis of GDP-GlcN (IV) was accomplished using a 12 ml reaction containing 50 mM Tris pH 7.5, 1 mM GTP, 1 mM MgCl$_2$, 0.8 U ml$^{-1}$ pyrophosphatase, 1.2 mM GlcN-1-P (III) and approximately 4.8 mg of His$_6$PtmE. The large-scale enzymatic synthesis of GDP-GlcNAc was performed similar to that above, except the scale was increased five-fold and GlcNAc-1-P was used in place of GlcN-1-P (III). Assessment of His$_6$PtmE substrate specificity was accomplished using 9 reactions, 80 μl each, containing 50 mM Tris pH 7.5, 2 mM MgCl$_2$, 50 μg His$_6$PtmE, and various combinations of 10 mM sugar-1-P (GalN-1-P, GlcN-1-P or GlcNAc-1-P) and 0.2 mM NTP (CTP, GTP, or TTP). Conversion of GDP-GlcN to GDP-GlcNAc. The His$_6$GlmU reaction was performed using 1 mM GDP-GlcN (IV), 1.2 mM acetyl-CoA and His$_6$GlmU in 25 mM sodium phosphate pH 7.8, 25 mM NaCl, 10 mM β-mercaptoethanol. In addition, a control reaction was performed containing 1 mM GlcN-1-P (III) instead of IV. Biosynthesis of legionaminic acid from GDP-GlcNAc. The stepwise enzymatic synthesis of intermediates 'or products was accomplished in 2 stages (V→VI→VII→VIII, and then VIII→IX→X) using 1 mM of V, 0.5 mM NAD, 0.8 mM PLP, 8 mM L-Glu, 1.2 mM acetyl-CoA, 1.2 mM PEP, LegBHis$_6$, His$_6$LegC, His$_6$LegH, His$_6$LegG, and His$_6$LegI as appropriate, in 25 mM sodium phosphate pH 7.3, 25 mM NaCl. Assessment of His$_6$LegG activity involved monitoring the reaction kinetics by $^1$H NMR (see NMR spectroscopy) for 75 min using 0.75 mM GDP-2, 4-diacetamido-2,4,6-trideoxy-α-D-Glc (VIII), 4 μg His$_6$LegG in 200 μl of 25 mM sodium phosphate pH 7.3, 25 mM NaCl at 25° C. In addition, the substrate flexibility of His$_6$LegG was assessed using a 300 μl reaction containing 40 μg His$_6$LegG, 25 mM sodium phosphate pH 7.3, 25 mM NaCl, and 0.75 mM UDP-2,4-diacetamido-2,4,6-trideoxy-α-D-Glc, with incubation at 37° C. for 1.5 h, and then overnight at 25° C. Biosynthesis of CMP-legionaminic acid. The CMP-activation of legionaminic acid (X→XI) was performed using a 20 ml reaction containing approximately 0.2 mM of X, 50 mM MgCl$_2$, 3 mM CTP, and 15 mg of LegFHis$_6$ in 25 mM sodium phosphate pH 7.8, 25 mM NaCl, with incubation at 37° C. for 5 h, and then 25° C. for 72 h. Metabolite purification. Typically, reactions were passed through an Amicon Ultra-15 (10,000 molecular weight cut-off) or Ultra-4 (5,000 molecular weight cut-off) filter membrane before analysis. As required, NDP-sugar preparations (GDP-Glc, GDP-GlcN, GDP-GlcNAc, CDP-GlcNAc, TDP-GlcNAc, and CMP-Leg) were lyophilized and desalted/purified using a Superdex Peptide 10/300 GL (Amersham Biosciences) column in 25 mM ammonium bicarbonate, pH 7.9. For further purity, the NDP-sugar samples above were subjected to anion-exchange chromatography (Mono Q 4.6/100 PE, Amersham Biosciences) using ammonium bicarbonate pH 7.9. Quantification of NDP-sugar preparations was determined using the molar extinction coefficients of CMP ($\epsilon_{260}$=7,400), GDP ($\epsilon_{260}$=11,500), TDP ($\epsilon_{260}$=8,700), and UDP ($\epsilon_{260}$=10,000).

CE and CE-MS Analysis

CE analysis was performed using either a P/ACE 5510 or P/ACE MDQ system (Beckman Instruments, Mississauga, Ont) with diode array detection. The capillaries were bare silica 50 μm×50 cm, with a detector at 50 cm, and the running buffer was 25 mM sodium tetraborate pH 9.4. Samples were introduced by pressure injection for 6 sec, and the separation was performed at 18 kV for 20 min. Peak integration was done using the Beckman P/ACE station software.

CE-MS was performed using a Prince CE system (Prince Technologies) coupled to a 4000 QTRAP mass spectrometer (Applied Biosystems/MDS Sciex). Separations were obtained on an ~90 cm bare silica capillary using 30 mM morpholine in deionized water, pH 9. A separation voltage of 20 kV, together with a pressure of 500 mbar was used for fast CE-MS analysis. The −5.2 kV electrospray ionization voltage was used for negative ion mode detection.

NMR Spectroscopy

Enzymatic reactions were carried out in 3 mm NMR tubes at 25° C. in 10% D$_2$O, and were monitored through the acquisition of $^1$H spectrum at various time intervals (indicated in min) using a Varian Inova 500 MHz ($^1$H) spectrometer with a Varian Z-gradient 3 mm probe. For structural characterization of compounds, filtered enzymatic reactions or purified material was exchanged into 100% D$_2$O. Structural analysis was performed using a Varian 600 MHz (1H) spectrometer with a Varian 5 mm Z-gradient triple resonance cryogenically cooled probe for optimal sensitivity. All spectra were referenced to an internal acetone standard ($\delta_H$ 2.225 ppm and $\delta_C$ 31.07 ppm).

While the preferred embodiments of the invention have been described above, it will be recognized and understood that various modifications may be made therein, and the appended claims are intended to cover all such modifications which may fall within the spirit and scope of the invention.

References

Angström J, Teneberg S, Karlsson K A. 1994. Delineation and comparison of ganglioside-binding epitopes for the toxins of *Vibrio cholerae, Escherichia coli,* and *Clostridium tetani:* evidence for overlapping epitopes. *Proc Natl Acad Sci USA.* 91:11859-11863.

Bork K, Gagiannis D, Orthmann A, Weidemann W, Kontou M, Reutter W, Horstkorte R. 2007. Experimental approaches to interfere with the polysialylation of the neural cell adhesion molecule in vitro and in vivo. *J Neurochem.* 103:65-71.

Buse M G, Robinson K A, Marshall B A, Mueckler, M. 1996. Differential effects of GLUT1 or GLUT4 overexpression on hexosamine biosynthesis by muscles of transgenic mice. *J Biol Chem.* 271:23197-23202.

Cazalet C, Jarraud S, Ghavi-Helm Y, Kunst F, Glaser P, Etienne J, Buchrieser C. 2008. Multigenome analysis identifies a worldwide distributed epidemic *Legionella pneumophila* clone that emerged within a highly diverse species. *Genome Res.* 18:431-441.

Crocker P R, Paulson J C, Varki A. 2007. Siglecs and their roles in the immune system. *Nat Rev Immunol.* 7:255-266.

Delputte P L, Van Breedam W, Delrue I, Oetke C, Crocker P R, Nauwynck H J. 2007. Porcine arterivirus attachment to the macrophage-specific receptor sialoadhesin is dependent on the sialic acid-binding activity of the N-terminal immunoglobulin domain of sialoadhesin. *J Virol.* 81:9546-9550.

Fernandez-Moreira E, Helbig J H, Swanson M S. 2006. Membrane vesicles shed by *Legionella pneumophila* inhibit fusion of phagosomes with lysosomes. *Infect Immun.* 74:3285-3295.

Glaze P A, Watson D C, Young N M, Tanner M E. 2008. Biosynthesis of CMP-N,N'-Diacetyllegionaminic Acid from UDP-N,N'-Diacetylbacillosamine in *Legionella pneumophila. Biochemistry.* 47:3272-3282.

Hausman S Z, Burns D L. 1993. Binding of pertussis toxin to lipid vesicles containing glycolipids. *Infect Immun.* 61:335-337.

Hedlund M, Ng E, Varki A, Varki N M. 2008. α2-6-Linked sialic acids on N-glycans modulate carcinoma differentiation in vivo. *Cancer Res.* 68:388-394.

Hsu K L, Pilobello K T, Mahal L K. 2006. Analyzing the dynamic bacterial glycome with a lectin microarray approach. *Nat Chem Biol.* 2:153-157.

Jolly L, Ferrari P, Blanot D, van Heijenoort J, Fassy F, Mengin-Lecreulx D. 1999. Reaction mechanism of phosphoglucosamine mutase from *Escherichia coli. Eur J Biochem.* 262:202-210.

Knirel Y A, Rietschel E T, Marre R, Zähringer U. 1994. The structure of the O-specific chain of *Legionella pneumophila* serogroup 1 lipopolysaccharide. *Eur J Biochem.* 221:239-245.

Knirel Y A, Shashkov A S, Tsvetkov Y E, Jansson P E, Zähringer U. 2003. 5,7-diamino-3,5,7,9-tetradeoxynon-2-ulosonic acids in bacterial glycopolymers: chemistry and biochemistry. *Adv Carbohydr Chem Biochem.* 58:371-417.

Kooistra O, Lüneberg E, Knirel Y A, Frosch M, Zähringer U. 2002. N-Methylation in polylegionaminic acid is associated with the phase-variable epitope of *Legionella pneumophila serogroup* 1 lipopolysaccharide. Identification of 5-(N,N-dimethylacetimidoyl)amino and 5-acetimidoyl(N- methyl)amino-7-acetamido-3,5,7,9-tetradeoxynon-2-ulosonic acid in the O-chain polysaccharide. Eur J Biochem. 269:560-572.

Lehmann F, Tiralongo E, Tiralongo J. 2006. Sialic acid-specific lectins: occurrence, specificity and function. Cell Mol Life Sci. 63:1331-1354.

Lundgren B R, Boddy C N. 2007. Sialic acid and N-acyl sialic acid analog production by fermentation of metabolically and genetically engineered Escherichia coli. Org Biomol Chem. 5:1903-1909.

McNally D J, Aubry A J, Hui J P, Khieu N H, Whitfield D, Ewing C P, Guerry P, Brisson J-R, Logan S M, Soo E C. 2007. Targeted metabolomics analysis of Campylobacter coli VC167 reveals legionaminic acid derivatives as novel flagellar glycans. J Biol Chem. 282:14463-14475.

Mengin-Lecreulx D, van Heijenoort J. 1994. Copurification of glucosamine-1-phosphate acetyltransferase and N-acetylglucosamine-1-phosphate uridyltransferase activities of Escherichia coli: characterization of the glmU gene product as a bifunctional enzyme catalyzing two subsequent steps in the pathway for UDP-N-acetylglucosamine synthesis. J Bacteriol. 176:5788-5795.

Mengin-Lecreulx D, van Heijenoort J. 1996. Characterization of the essential gene glmM encoding phosphoglucosamine mutase in Escherichia coli. J Biol Chem. 271:32-39.

Merritt E A, Kuhn P, Sarfaty S, Erbe J L, Holmes R K, Hol W G. 1998. The 1.25 A resolution refinement of the cholera toxin B-pentamer: evidence of peptide backbone strain at the receptor-binding site. J Mol Biol. 282:1043-1059.

Mouilleron S, Badet-Denisot M A, Golinelli-Pimpaneau B. 2006. Glutamine binding opens the ammonia channel and activates glucosamine-6P synthase. J Biol Chem. 281:4404-4412.

Olivier N B, Chen M M, Behr J R, Imperiali B. 2006. In vitro biosynthesis of UDP-N,N'-diacetylbacillosamine by enzymes of the Campylobacter jejuni general protein glycosylation system. Biochemistry. 45:13659-13669.

Pompeo F, Bourne Y, van Heijenoort J, Fassy F, Mengin-Lecreulx D. 2001. Dissection of the bifunctional Escherichia coli N-acetylglucosamine-1-phosphate uridyltransferase enzyme into autonomously functional domains and evidence that trimerization is absolutely required for glucosamine-1-phosphate acetyltransferase activity and cell growth. J Biol Chem. 276:3833-3839.

Pontes de Carvalho L C, Tomlinson S, Vandekerckhove F, Bienen E J, Clarkson A B, Jiang M S, Hart G W, Nussenzweig V. 1993. Characterization of a novel trans-sialidase of Trypanosoma brucei procyclic trypomastigotes and identification of procyclin as the main sialic acid acceptor. J Exp Med. 177:465-474.

Schoenhofen I C, Lunin V V, Julien J P, Li Y, Ajamian E, Matte A, Cygler M, Brisson J-R, Aubry A, Logan S M, et al. 2006. Structural and functional characterization of PseC, an aminotransferase involved in the biosynthesis of pseudaminic acid, an essential flagellar modification in Helicobacter pylori. J Biol Chem. 281:8907-8916.

Schoenhofen I C, McNally D J, Brisson J R, Logan S M. 2006. Elucidation of the CMP-pseudaminic acid pathway in Helicobacter pylori: synthesis from UDP-N-acetylglucosamine by a single enzymatic reaction. Glycobiology. 16:8C-14C.

Schoenhofen I C, McNally D J, Vinogradov E, Whitfield D, Young N M, Dick S, Wakarchuk W W, Brisson J-R, Logan S M. 2006. Functional characterization of dehydratase/aminotransferase pairs from Helicobacter and Campylobacter: enzymes distinguishing the pseudaminic acid and bacillosamine biosynthetic pathways. J Biol Chem. 281:723-732.

Seven E, Hood D W, Thomas, G H. 2007. Sialic acid utilization by bacterial pathogens. Microbiology. 153:2817-2822.

Silva E, Marques A R, Fialho A M, Granja A T, Sá-Correia I. 2005. Proteins encoded by Sphingomonas elodea ATCC 31461 rmlA and ugpG genes, involved in gellan gum biosynthesis, exhibit both dTDP- and UDP-glucose pyrophosphorylase activities. Appl Environ Microbiol. 71:4703-4712.

Stein P E, Boodhoo A, Armstrong G D, Heerze L D, Cockle S A, Klein M H, Read R J. 1994. Structure of a pertussis toxin-sugar complex as a model for receptor binding. Nat Struct Biol. 1:591-596.

Teplyakov A, Obmolova G, Badet-Denisot M A, Badet B. 1999. The mechanism of sugar phosphate isomerization by glucosamine 6-phosphate synthase. Protein Sci. 8:596-602.

Tsvetkov Y E, Shashkov A S, Knirel Y A, Zähringer U. 2001. Synthesis and identification in bacterial lipopolysaccharides of 5,7-diacetamido-3,5,7,9-tetradeoxy-D-glycero-D-galacto- and -D-glycero-D-talo-non-2-ulosonic acids. Carbohydr Res. 331:233-237.

Varki A. 2007. Glycan-based interactions involving vertebrate sialic-acid-recognizing proteins. Nature. 446:1023-1029.

Varki A and Angata T. 2006. Siglecs--the major subfamily of I-type lectins. Glycobiology. 16:1 R-27R.

Varki N M and Varki A. 2007. Diversity in cell surface sialic acid presentations: implications for biology and disease. Lab Invest. 87:851-857.

Yu V L, Plouffe J F, Pastoris M C, Stout J E, Schousboe M, Widmer A, Summersgill J, File T, Heath C M, Paterson D L, et al. 2002. Distribution of Legionella species and serogroups isolated by culture in patients with sporadic community-acquired legionellosis: an international collaborative survey. J Infect Dis. 186:127-128.

TABLE 1

NMR chemical shifts δ (ppm) for the sugars of compounds V to XI.

| Compound | $^1$H | $\delta_H$ (ppm) | $^{13}$C | $\delta_C$ (ppm) |
|---|---|---|---|---|
| V | H1 | 5.51 | C1 | 95.1 |
| | H2 | 3.99 | C2 | 54.5 |
| | H3 | 3.81 | C3 | 71.7 |
| | H4 | 3.55 | C4 | 70.3 |
| | H5 | 3.92 | C5 | 73.8 |
| | H6 | 3.82/3.86 | C6 | 61.2 |
| VI | H1 | 5.45 | C1 | 95.3 |
| | H2 | 4.10 | C2 | 53.5 |
| | H3 | 3.82 | C3 | 72.4 |
| | H5 | 4.11 | C5 | 70.9 |
| | H6 | 1.21 | C6 | 12.4 |
| VII | H1 | 5.50 | C1 | 95.6 |
| | H2 | 4.06 | C2 | 55.0 |
| | H3 | 3.87 | C3 | 69.1 |
| | H4 | 2.96 | C4 | 58.6 |
| | H5 | 4.21 | C5 | 68.0 |
| | H6 | 1.32 | C6 | 18.0 |
| VIII | H1 | 5.50 | C1 | 95.4 |
| | H2 | 4.05 | C2 | 55.2 |
| | H3 | 3.80 | C3 | 69.8 |
| | H4 | 3.68 | C4 | 57.9 |
| | H5 | 4.05 | C5 | 69.3 |
| | H6 | 1.16 | C6 | 18.0 |
| | | α/β | | α/β |

TABLE 1-continued

NMR chemical shifts δ (ppm) for the sugars of compounds V to XI.

| Compound | $^1H$ | $\delta_H$ (ppm) | $^{13}C$ | $\delta_C$ (ppm) |
|---|---|---|---|---|
| IX | H1 | 5.11/4.96 | C1 | 94.0/94.0 |
|  | H2 | 4.30/4.46 | C2 | 53.8/54.8 |
|  | H3 | 4.06/3.84 | C3 | 67.7/71.7 |
|  | H4 | 3.77/3.66 | C4 | 54.8/54.5 |
|  | H5 | 3.97/3.51 | C5 | 68.1/72.6 |
|  | H6 | 1.19/1.21 | C6 | 18.0/18.0 |
| X | H3a | 1.83 | C3 | 40.8 |
|  | H3e | 2.22 |  |  |
|  | H4 | 3.96 | C4 | 68.5 |
|  | H5 | 3.72 | C5 | 53.8 |
|  | H6 | 4.24 | C6 | 70.4 |
|  | H7 | 3.86 | C7 | 54.3 |
|  | H8 | 3.86 | C8 | 67.5 |
|  | H9 | 1.16 | C9 | 20.4 |
| XI | H3a | 1.63 ($J_{3a,4}$ 11.9; $J_{3a,P}$ 5.8) | C3 | 42.6 |
|  | H3e | 2.48 ($J_{3e,4}$ 4.7; $J_{3e,3a}$ 13.4) |  |  |
|  | H4 | 3.98 ($J_{4,5}$ 10.3) | C4 | 68.3 |
|  | H5 | 3.72 ($J_{5,6}$ 10.3) | C5 | 53.7 |
|  | H6 | 4.33 ($J_{6,7}$ 1.5) | C6 | 72.3 |
|  | H7 | 3.77 ($J_{7,8}$ 9.5) | C7 | 55.3 |
|  | H8 | 4.03 ($J_{8,9}$ 6.4) | C8 | 66.9 |
|  | H9 | 1.10 | C9 | 19.5 |

TABLE 2

Enzymes functionally characterized in this study. The enzymes involved in CMP-legionaminic acid biosynthesis are shown in sequential order, where each product is a substrate for the next biosynthetic step. The initial substrate for the pathway is Fructose-6-P (I).

| Cj number | Recommended Nomenclature | Previous Nomenclature(s) | In vitro Enzyme function | Biosynthetic product(s) |
|---|---|---|---|---|
| Cj1330 | PtmF | PtmF | isomerase | GlcN-6-P (II) |
| Cj1332 | PtmA | PtmA | glutaminase |  |
| Cj1407c | PgmL |  | phosphoglucosamine mutase | GlcN-1-P (III) |
| Cj1329 | PtmE | PtmE | GlcN-1-P guanylyltransferase | GDP-GlcN (IV) |
| Cj0821 | GlmU | GlmU | N-acetyltransferase | GDP-GlcNAc (V) |
| Cj1319 | LegB |  | 4,6-dehydratase | GDP-2-acetamido-2,6-dideoxy-α-D-xylo-hexos-4-ulose (VI) |
| Cj1320 | LegC |  | aminotransferase | GDP-4-amino-4,6-dideoxy-α-D-GlcNAc (VII) |
| Cj1298 | LegH |  | N-acetyltransferase | GDP-2,4-diacetamido-2,4,6-trideoxy-α-D-Glc (VIII) |
| Cj1328 | LegG | NeuC2, PtmD | 2-epimerase/NDP-sugar hydrolase | 2,4-diacetamido-2,4,6-trideoxy-D-Man (IX) |
| Cj1327 | LegI | NeuB2, PtmC | Leg synthase | 5,7-diacetamido-3,5,7,9-tetradeoxy-D-glycero-β-D-galacto-nonulosonic acid (X, Leg) |
| Cj1331 | LegF | NeuA3, PtmB | CMP-Leg synthetase | CMP-Leg (XI) |

TABLE 3

Enzyme descriptions for FIG. 3.

| Number | Cj number | Gene name | Enzyme function |
|---|---|---|---|
| 1 | 1366c | glmS | glucosamine-6-P synthase |
| 2 | 1330 | ptmF | isomerase |
| 3 | 1332 | ptmA | glutaminase (2 and 3 equivalent to 1) |
| 4 | 0360 | glmM | phosphoglucosamine mutase |
| 5 | 1407c | pgmL | phosphoglucosamine mutase |
| 6 | 0821 | glmU | nucleotidyltransferase/N-acetyltransferase |
| 7 | 1142 | neuC1 | hydrolyzing 2-epimerase |
| 8 | 1141 | neuB1 | sialic acid synthase |
| 9 | 1143 | neuA1 | CMP-sialic acid synthetase |
| 10 | 1140 | cstIII | sialyltransferase |
| 11 | 1120c | pglF | dehydratase |
| 12 | 1121c | pglE | aminotransferase |
| 13 | 1123c | pglD | N-acetyltransferase |
| 14 | 1124c | pglC | glycosyltransferase |
| 15 | 1125c | pglA | glycosyltransferase |
| 16 | 1127c | pglJ | glycosyltransferase |
| 17 | 1129c | pglH | glycosyltransferase |
| 18 | 1128c | pglI | glycosyltransferase |
| 19 | 1130c | pglK | flippase |
| 20 | 1126c | pglB | oligosaccharyltransferase |
| 21 | 0858c | murA | enolpyruvyl transferase |
| 22 | 1676 | murB | reductase |
| 23 | 1054c | murC | L-Ala ligase |
| 24 | 0432c | murD | D-Glu ligase |
| 25 | 1641 |  murE | L-Lys (or $A_2$pm) ligase |
| 26 | 0795c | murF | D-Ala-D-Ala ligase |
| 27 | 0433c | mraY | glycosyltransferase (lipid I synthase) |
| 28 | 1039 | murG | glycosyltransferase (lipid II synthase) |
| 29 | 1293 | pseB | dehydratase/epimerase |
| 30 | 1294 | pseC | aminotransferase |
| 31 | 1313 | pseH | N-acetyltransferase |
| 32 | 1312 | pseG | UDP-sugar hydrolase |
| 33 | 1317 | pseI | pseudaminic acid synthase |
| 34 | 1311 | pseF | CMP-pseudaminic acid synthetase |
| 35 | 1329 | ptmE | nucleotidyltransferase |
| 36 | 1319 | legB | dehydratase |
| 37 | 1320 | legC | aminotransferase |
| 38 | 1298 | legH | N-acetyltransferase |
| 39 | 1328 | legG | hydrolyzing 2-epimerase |
| 40 | 1327 | legI | legionaminic acid synthase |
| 41 | 1331 | legF | CMP-legionaminic acid synthetase |

TABLE 4

Alternate carbohydrate nomenclature for FIG. 3.
CMP, cytidine-5'-monophosphate; GDP, guanosine-5'-diphosphate; UDP, uridine-5'-diphosphate

| Abbreviated Carbohydrate Nomenclature | Full Carbohydrate Nomenclature |
|---|---|
| (I) Fru-6-P | D-fructose-6-phosphate |
| (II) GlcN-6-P | D-glucosamine-6-phosphate |
| (III) GlcN-1-P | α-D-glucosamine-1-phosphate |
| GlcNAc-1-P | N-acetyl-α-D-glucosamine-1-phosphate |
| UDP-GlcNAc | UDP-N-acetyl-α-D-glucosamine |
| ManNAc | N-acetyl-D-mannosamine |
| Sia | 5-acetamido-3,5-dideoxy-D-glycero-β-D-galacto-nonulosonic acid (sialic acid) |
| CMP-Sia | CMP-5-acetamido-3,5-dideoxy-D-glycero-β-D-galacto-nonulosonic acid (CMP-sialic acid) |
| UDP-4-keto-6-deoxy-GlcNAc | UDP-2-acetamido-2,6-dideoxy-α-D-xylo-hexos-4-ulose |
| UDP-4-amino-6-deoxy-GlcNAc | UDP-4-amino-4,6-dideoxy-N-acetyl-α-D-glucosamine |
| UDP-2,4-diNAc-6-deoxy-Glc | UDP-2,4-diacetamido-2,4,6-trideoxy-α-D-glucose |
| UDP-4-keto-6-deoxy-AltNAc | UDP-2-acetamido-2,6-dideoxy-β-L-arabino-hexos-4-ulose |
| UDP-4-amino-6-deoxy-AltNAc | UDP-4-amino-4,6-dideoxy-N-acetyl-β-L-altrosamine |
| UDP-2,4-diNAc-6-deoxy-Alt | UDP-2,4-diacetamido-2,4,6-trideoxy-β-L-altrose |
| 2,4-diNAc-6-deoxy-Alt | 2,4-diacetamido-2,4,6-trideoxy-L-altrose |
| Pse | 5,7-diacetamido-3,5,7,9-tetradeoxy-L-glycero-α-L-manno-nonulosonic acid (pseudaminic acid) |
| CMP-Pse | CMP-5,7-diacetamido-3,5,7,9-tetradeoxy-L-glycero-α-L-manno-nonulosonic acid (CMP-pseudaminic acid) |
| (IV) GDP-GlcN | GDP-α-D-glucosamine |
| (V) GDP-GlcNAc | GDP-N-acetyl-α-D-glucosamine |
| (VI) GDP-4-keto-6-deoxy-GlcNAc | GDP-2-acetamido-2,6-dideoxy-α-D-xylo-hexos-4-ulose |
| (VII) GDP-4-amino-6-deoxy-GlcNAc | GDP-4-amino-4,6-dideoxy-N-acetyl-α-D-glucosamine |
| (VIII) GDP-2,4-diNAc-6-deoxy-Glc | GDP-2,4-diacetamido-2,4,6-trideoxy-α-D-glucose |
| (IX) 2,4-diNAc-6-deoxy-Man | 2,4-diacetamido-2,4,6-trideoxy-D-mannose |
| (X) Leg | 5,7-diacetamido-3,5,7,9-tetradeoxy-D-glycero-β-D-galacto-nonulosonic acid (legionaminic acid) |
| (XI) CMP-Leg | CMP-5,7-diacetamido-3,5,7,9-tetradeoxy-D-glycero-β-D-galacto-nonulosonic acid (CMP-legionaminic acid) |

TABLE 5

NMR chemical shifts δ (ppm) for the sugars of compounds IV, as well as GDP-α-D-Glc, CDP-α-D-GlcNAc and TDP-α-D-GlcNAc.

| Compound | $^1$H | $\delta_H$ (ppm) | $^{13}$C | $\delta_C$ (ppm) |
|---|---|---|---|---|
| IV | H1 | 5.56 | C1 | 97.3 |
|  | H2 | 2.76 | C2 | 56.3 |
|  | H3 | 3.63 | C3 | 74.3 |
|  | H4 | 3.44 | C4 | 70.5 |
|  | H5 | 3.89 | C5 | 74.3 |
|  | H6 | 3.74, 3.84 | C6 | 61.4 |
| Guanine: 8.1-138.5; 117.3; 153.8 ppm | | | | |
| GDP-Glc | H1 | 5.58 | C1 | 96.6 |
|  | H2 | 3.50 | C2 | 72.7 |
|  | H3 | 3.88 | C3 | 73.9 |
|  | H4 | 3.43 | C4 | 70.5 |
|  | H5 | 3.76 | C5 | 73.9 |
|  | H6 | 3.73, 3.83 | C6 | 61.5 |
| Guanine: 8.09-138.4; 117.3; 152.7 ppm | | | | |
| CDP-GlcNAc | H1 | 5.52 | C1 | 95.7 |
|  | H2 | 3.99 | C2 | 54.8 |
|  | H3 | 3.81 | C3 | 72.1 |
|  | H4 | 3.55 | C4 | 70.7 |
|  | H5 | 3.92 | C5 | 74.1 |
|  | H6 | 3.80, 3.86 | C6 | 61.4 |
| Cytidine: 6.12-97.7; 7.94; acetate 2.07/23.3 ppm | | | | |
| TDP-GlcNAc | H1 | 5.51 | C1 | 95.8 |
|  | H2 | 3.99 | C2 | 54.8 |
|  | H3 | 3.81 | C3 | 72.1 |
|  | H4 | 3.55 | C4 | 70.7 |
|  | H5 | 3.93 | C5 | 74.1 |
|  | H6 | 3.81, 3.86 | C6 | 61.5 |
| Thymidine: H-6: 7.73; Me 1.94-12.7; N-acetate 2.08/23.3 ppm | | | | |

TABLE 6

Plasmids used in this study.

| Plasmid | Description | Source/Reference |
|---|---|---|
| pCR2.1 | Ap$^r$, Kn$^r$, oriColE1, lac promoter, used for cloning | Invitrogen |
| pET30a | Kn$^r$, oriColE1, T7 promoter, used for C-terminal His$_6$-tagged protein expression | Novagen |
| pFO4 | pET15b derivative; Ap$^r$, oriColE1, T7 promoter, used for N-terminal His$_6$-tagged protein expression | Schoenhofen et al., 2006a |
| pNRC145.3 | cj1330 BamHI-EcoRI in pFO4, encodes for C. jejuni His$_6$PtmF | This study |
| pNRC141.1 | cj1332 NdeI-XhoI in pET30a, encodes for C. jejuni PtmAHis$_6$ | This study |
| pNRC173.1 | cj1407c NdeI-XhoI in pET30a, encodes for C. jejuni PgmLHis$_6$ | This study |
| pNRC136.1 | cj1329 BamHI-EcoRI in pFO4, encodes for C. jejuni His$_6$PtmE | This study |
| pNRC175.1 | cj0821 BamHI-EcoRI in pFO4, encodes for C. jejuni His$_6$GlmU | This study |
| pNRC16.1 | cj1319 NdeI-XhoI in pET30a, encodes for C. jejuni LegBHis$_6$ | This study |
| pNRC83.1 | cj1320 BamHI-EcoRI in pFO4, encodes for C. jejuni His$_6$LegC | This study |
| pNRC164.3 | cj1298 BamHI-EcoRI in pFO4, encodes for C. jejuni His$_6$LegH | This study |
| pNRC134.1 | cj1328 BamHI-EcoRI in pFO4, encodes for C. jejuni His$_6$LegG | This study |
| pNRC51.1 | cj1327 BamHI-EcoRI in pFO4, encodes for C. jejuni His$_6$LegI | This study |
| pNRC139.1 | cj1331 NdeI-XhoI in pET30a, encodes for C. jejuni LegFHis$_6$ | This study |
| pNRC152.1 | cj1123c NdeI-XhoI in pET30a, encodes for C. jejuni PglDHis$_6$ | This study |

TABLE 7

Oligonucleotides used in this study.

| Oligo | Sequence (5' → 3') | Purpose |
|---|---|---|
| NRC239 | GGATCCAAAGTCTTAATCATAGGCTTTGGAAGC [SEQ ID NO: 1] | Cloning of |
| NRC240 | GAATTCTCAGCCATTTTTTTTCCTTACTTCATC [SEQ ID NO: 2] | pNRC145.3 |
| NRC231 | CATATGCTTGAAAATAAAATCATCTTTGTAGCAG [SEQ ID NO: 3] | Cloning of |
| NRC232 | CTCGAGTAAGCCCCATCCATCATCTACC [SEQ ID NO: 4] | pNRC141.1 |
| NRC300 | CATATGAATTTGAAGGAAAAAATGTTAGATGTGATTTTTAG [SEQ ID NO: 5] | Cloning of |
| NRC301 | CTCGAGATTCTTAAATCTAGCTTTTATATCATTAAACAAAGTAAATAC [SEQ ID NO: 6] | pNRC173.1 |
| NRC221 | GGATCCGATATAAACAAACTCAAACTCACCCC [SEQ ID NO: 7] | Cloning of |
| NRC222 | GAATTCTCATTTAAAATCCTCATTGGCTTTTAAAAAC [SEQ ID NO: 8] | pNRC136.1 |
| NRC296 | GGATCCAAAACTTCTATTTTGATTTTAGCGGCAGG [SEQ ID NO: 9] | Cloning of |
| NRC297 | GAATTCTCATTTTTGAAATTTCTTATAATAATAATCTTTTATCATTTTATG [SEQ ID NO: 10] | pNRC175.1 |
| NRC39 | CATATGAGAAATATTTTAGTTACAGGTGC [SEQ ID NO: 11] | Cloning of |
| NRC40 | CTCGAGAACATTATAAAGCTCGCTTTTATAATTTTC [SEQ ID NO: 12] | pNRC16.1 |
| NRC139 | GGATCCATGTTTAAAAAAGAAATTTCTTTTATAAAAAGTC [SEQ ID NO: 13] | Cloning of |
| NRC140 | GAATTCTCATTCCTTTTTATTTGCTATTCTAAC [SEQ ID NO: 14] | pNRC83.1 |
| NRC280 | GGATCCAAATATTTACTTGAATTTGAAAATAAAAAATACTCCAC [SEQ ID NO: 15] | Cloning of |
| NRC281 | GAATTCTTAATATATTGTATCATAATTTTCTATTAGAATTGTTTGG [SEQ ID NO: 16] | pNRC164.3 |
| NRC217 | GGATCCAGTAAAAGAAAAATTTGTATAGTCAGTGCAAC [SEQ ID NO: 17] | Cloning of |
| NRC218 | GAATTCTTATAAATCGATGAAATTTTTATGTAAAATTGTATC [SEQ ID NO: 18] | pNRC134.1 |
| NRC99 | GGATCCATGAAAAAAACTTTAATCATCGCAGAAG [SEQ ID NO: 19] | Cloning of |
| NRC100 | GAATTCTTACTCACGGATAAGCTCATCTTC [SEQ ID NO: 20] | pNRC51.1 |
| NRC227 | CATATGGCTGAAATTTTATGTACTATTTGTGC [SEQ ID NO: 21] | Cloning of |
| NRC228 | CTCGAGAAAATCCTTTGGCGATAAATTTTTTAAAGAG [SEQ ID NO: 22] | pNRC139.1 |
| NRC253 | CATATGGCAAGAACTGAAAAAATTTATATTTATGGTG [SEQ ID NO: 23] | Cloning of |
| NRC254 | CTCGAGCATCCTTTTTGCAGGTACTCCC [SEQ ID NO: 24] | pNRC152.1 |
| T7-F | TAATACGACTCACTATAGGG [SEQ ID NO: 25] | Sequencing |
| T7-R | GCTAGTTATTGCTCAGCGG [SEQ ID NO: 26] | of pET30a constructs |
| NRC175 | TTAATACGACTCACTATAGGGGAATTG [SEQ ID NO: 27] | Sequencing |
| NRC160 | GGTTATGCTAGTTATTGCTCAGCGG [SEQ ID NO: 28] | of pFO4 constructs |

The invention claimed is:
1. A method of synthesis comprising:
   (a) providing a reaction vessel comprising GDP-N-acetyl-glucosamine, nicotinamide adenine dinucleotide (NAD) and LegB; and
   (b) recovering GDP-2-acetamido-2,6-dideoxy-α-D-xylo-hexos-4-ulose.
2. The method of claim 1, wherein the reaction vessel further comprises LegC, pyridoxal-phosphate (PLP), and an amino donor, and wherein GDP-4-amino-4,6-dideoxy-α-D-GlcNAc is recovered.
3. The method of claim 2, wherein the reaction vessel further comprises an N-acetyltransferase and acetyl-CoA, and wherein GDP-2,4-diacetamido-2,4,6-trideoxy-α-D-Glc is recovered.
4. The method of claim 3, wherein the N-acetyltransferase is LegH.
5. The method of claim 3 or 4, wherein the reaction vessel further comprises LegG and water, and wherein 2,4-diacetamido-2,4,6-trideoxy-D-Man is recovered.
6. The method of claim 5, wherein the reaction vessel further comprises LegI and phosphoenol pyruvate (PEP), and wherein legionaminic acid is recovered.
7. The method of claim 6, wherein the reaction vessel further comprises LegF, cytidine triphosphate (CTP), and $Me^{2+}$, and wherein CMP-legionaminic acid is recovered.
8. A method of synthesis comprising:
   (a) providing a reaction vessel comprising GDP-2-acetamido-2,6-dideoxy-α-D-xylo-hexos-4-ulose, LegC, pyridoxal-phosphate (PLP) and an amino donor; and
   (b) recovering GDP-4-amino-4,6-dideoxy-α-D-GlcNAc.
9. The method of claim 8, wherein the reaction vessel further comprises an N-acetyltransferase and acetyl-CoA, and wherein GDP-2,4-diacetamido-2,4,6-trideoxy-α-D-Glc is recovered.
10. The method of claim 9, wherein the N-acetyltransferase is LegH.
11. The method of claim 9 or 10, wherein the reaction vessel further comprises LegG and water, and wherein 2,4-diacetamido-2,4,6-trideoxy-D-Man is recovered.
12. The method of claim 11, wherein the reaction vessel further comprises LegI and phosphoenol pyruvate (PEP), and wherein legionaminic acid is recovered.
13. The method of claim 12, wherein the reaction vessel further comprises LegF, cytidine triphosphate (CTP), and $Me^{2+}$, and wherein CMP-legionaminic acid is recovered.
14. A method of synthesis comprising:
   (a) providing a reaction vessel comprising GDP-2,4-diacetamido-2,4,6-trideoxy-α-D-Glc, LegG, and water; and
   (b) recovering 2,4-diacetamido-2,4,6-trideoxy-D-Man.
15. The method of claim 14, wherein the reaction vessel further comprises LegI and phosphoenol pyruvate (PEP), and wherein legionaminic acid is recovered.
16. The method of claim 15, wherein the reaction vessel further comprises LegF, cytidine triphosphate (CTP), and $Me^{2+}$, and wherein CMP-legionaminic acid is recovered.
17. A method of synthesis comprising:
   (a) providing a reaction vessel comprising GDP-4-amino-4,6-dideoxy-α-D-GlcNAc, an N-acetyltransferase, and acetyl-CoA; and
   (b) recovering GDP-2,4-diacetamido-2,4,6-trideoxy-α-D-Glc.
18. The method of claim 17, wherein the N-acetyltransferase is LegH.
19. The method of claim 17 or 18, wherein the reaction vessel further comprises LegG and water, and wherein 2,4-diacetamido-2,4,6-trideoxy-D-Man is recovered.
20. The method of claim 19, wherein the reaction vessel further comprises LegI and phosphoenol pyruvate (PEP), and wherein legionaminic acid is recovered.
21. The method of claim 20, wherein the reaction vessel further comprises LegF, cytidine triphosphate (CTP), and $Me^{2+}$, and wherein CMP-legionaminic acid is recovered.
22. A method of synthesis comprising:
   (a) providing a reaction vessel comprising GDP-N-acetyl-glucosamine, nicotinamide adenine dinucleotide (NAD), LegB, LegC, pyridoxal-phosphate (PLP), an amino donor, an N-acetyltransferase, acetyl-CoA, LegG, water, LegI, phosphoenol pyruvate (PEP), LegF, cytidine triphosphate (CTP), and $Me^{2+}$; and
   (b) recovering CMP-legionaminic acid.
23. The method of claim 22, wherein the N-acetyltransferase is LegH.

* * * * *

SEQUENCE LISTING

<160> NUMBER OF SEQ ID NOS: 30

<210> SEQ ID NO 1
<211> LENGTH: 33
<212> TYPE: DNA
<213> ORGANISM: Artificial Sequence
<220> FEATURE:
<223> OTHER INFORMATION: primer

<400> SEQUENCE: 1
ggatccaaag tcttaatcat aggctttgga agc                33

<210> SEQ ID NO 2
<211> LENGTH: 33
<212> TYPE: DNA
<213> ORGANISM: Artificial Sequence
<220> FEATURE:
<223> OTHER INFORMATION: primer

<400> SEQUENCE: 2
gaattctcag ccattttttt tccttacttc atc                                    33

<210> SEQ ID NO 3
<211> LENGTH: 34
<212> TYPE: DNA
<213> ORGANISM: Artificial Sequence
<220> FEATURE:
<223> OTHER INFORMATION: primer

<400> SEQUENCE: 3
catatgcttg aaaataaaat catctttgta gcag                                   34

<210> SEQ ID NO 4
<211> LENGTH: 28
<212> TYPE: DNA
<213> ORGANISM: Artificial Sequence
<220> FEATURE:
<223> OTHER INFORMATION: primer

<400> SEQUENCE: 4
ctcgagtaag ccccatccat catctacc                                          28

<210> SEQ ID NO 5
<211> LENGTH: 41
<212> TYPE: DNA
<213> ORGANISM: Artificial Sequence
<220> FEATURE:
<223> OTHER INFORMATION: primer

<400> SEQUENCE: 5
catatgaatt tgaaggaaaa aatgttagat gtgattttta g                           41

<210> SEQ ID NO 6
<211> LENGTH: 48
<212> TYPE: DNA
<213> ORGANISM: Artificial Sequence
<220> FEATURE:
<223> OTHER INFORMATION: primer

<400> SEQUENCE: 6
ctcgagattc ttaaatctag cttttatatc attaaacaaa gtaaatac                    48

<210> SEQ ID NO 7
<211> LENGTH: 32
<212> TYPE: DNA
<213> ORGANISM: Artificial Sequence
<220> FEATURE:
<223> OTHER INFORMATION: primer

<400> SEQUENCE: 7
ggatccgata taaacaaact caaactcacc cc                                     32

<210> SEQ ID NO 8
<211> LENGTH: 37
<212> TYPE: DNA
<213> ORGANISM: Artificial Sequence
<220> FEATURE:
<223> OTHER INFORMATION: primer

<400> SEQUENCE: 8
gaattctcat ttaaatcct cattggcttt taaaaac                                 37

<210> SEQ ID NO 9
<211> LENGTH: 35
<212> TYPE: DNA
<213> ORGANISM: Artificial Sequence
<220> FEATURE:
<223> OTHER INFORMATION: primer

<400> SEQUENCE: 9
ggatccaaaa cttctatttt gattttagcg gcagg     35

<210> SEQ ID NO 10
<211> LENGTH: 51
<212> TYPE: DNA
<213> ORGANISM: Artificial Sequence
<220> FEATURE:
<223> OTHER INFORMATION: primer

<400> SEQUENCE: 10
gaattctcat ttttgaaatt tcttataata ataatctttt atcattttat g     51

<210> SEQ ID NO 11
<211> LENGTH: 29
<212> TYPE: DNA
<213> ORGANISM: Artificial Sequence
<220> FEATURE:
<223> OTHER INFORMATION: primer

<400> SEQUENCE: 11
catatgagaa atattttagt tacaggtgc     29

<210> SEQ ID NO 12
<211> LENGTH: 36
<212> TYPE: DNA
<213> ORGANISM: Artificial Sequence
<220> FEATURE:
<223> OTHER INFORMATION: primer

<400> SEQUENCE: 12
ctcgagaaca ttataaagct cgcttttata attttc     36

<210> SEQ ID NO 13
<211> LENGTH: 40
<212> TYPE: DNA
<213> ORGANISM: Artificial Sequence
<220> FEATURE:
<223> OTHER INFORMATION: primer

<400> SEQUENCE: 13
ggatccatgt ttaaaaaaga aatttctttt ataaaaagtc     40

<210> SEQ ID NO 14
<211> LENGTH: 33
<212> TYPE: DNA
<213> ORGANISM: Artificial Sequence
<220> FEATURE:
<223> OTHER INFORMATION: primer

<400> SEQUENCE: 14
gaattctcat tcctttttat ttgctattct aac     33

<210> SEQ ID NO 15
<211> LENGTH: 40
<212> TYPE: DNA
<213> ORGANISM: Artificial Sequence
<220> FEATURE:
<223> OTHER INFORMATION: primer

<400> SEQUENCE: 15
ggatccatgt ttaaaaaaga aatttctttt ataaaaagtc                40

<210> SEQ ID NO 16
<211> LENGTH: 46
<212> TYPE: DNA
<213> ORGANISM: Artificial Sequence
<220> FEATURE:
<223> OTHER INFORMATION: primer

<400> SEQUENCE: 16
gaattcttaa tatattgtat cataattttc tattagaatt gtttgg         46

<210> SEQ ID NO 17
<211> LENGTH: 38
<212> TYPE: DNA
<213> ORGANISM: Artificial Sequence
<220> FEATURE:
<223> OTHER INFORMATION: primer

<400> SEQUENCE: 17
ggatccagta aagaaaaat ttgtatagtc agtgcaac                   38

<210> SEQ ID NO 18
<211> LENGTH: 42
<212> TYPE: DNA
<213> ORGANISM: Artificial Sequence
<220> FEATURE:
<223> OTHER INFORMATION: primer

<400> SEQUENCE: 18
gaattcttat aaatcgatga aatttttatg taaaattgta tc             42

<210> SEQ ID NO 19
<211> LENGTH: 34
<212> TYPE: DNA
<213> ORGANISM: Artificial Sequence
<220> FEATURE:
<223> OTHER INFORMATION: primer

<400> SEQUENCE: 19
ggatccatga aaaaacttt aatcatcgca gaag                       34

<210> SEQ ID NO 20
<211> LENGTH: 30
<212> TYPE: DNA
<213> ORGANISM: Artificial Sequence
<220> FEATURE:
<223> OTHER INFORMATION: primer

<400> SEQUENCE: 20
gaattcttac tcacggataa gctcatcttc                           30

<210> SEQ ID NO 21
<211> LENGTH: 32
<212> TYPE: DNA
<213> ORGANISM: Artificial Sequence
<220> FEATURE:
<223> OTHER INFORMATION: primer

<400> SEQUENCE: 21
catatggctg aaattttatg tactatttgt gc                        32

```
<210> SEQ ID NO 22
<211> LENGTH: 37
<212> TYPE: DNA
<213> ORGANISM: Artificial Sequence
<220> FEATURE:
<223> OTHER INFORMATION: primer

<400> SEQUENCE: 22
ctcgagaaaa tcctttggcg ataaattttt taaagag                           37

<210> SEQ ID NO 23
<211> LENGTH: 37
<212> TYPE: DNA
<213> ORGANISM: Artificial Sequence
<220> FEATURE:
<223> OTHER INFORMATION: primer

<400> SEQUENCE: 23
catatggcaa gaactgaaaa aatttatatt tatggtg                           37

<210> SEQ ID NO 24
<211> LENGTH: 28
<212> TYPE: DNA
<213> ORGANISM: Artificial Sequence
<220> FEATURE:
<223> OTHER INFORMATION: primer

<400> SEQUENCE: 24
ctcgagcatc cttttgcag gtactccc                                      28

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
taatacgact cactataggg                                              20

<210> SEQ ID NO 26
<211> LENGTH: 19
<212> TYPE: DNA
<213> ORGANISM: Artificial Sequence
<220> FEATURE:
<223> OTHER INFORMATION: primer

<400> SEQUENCE: 26
gctagttatt gctcagcgg                                               19

<210> SEQ ID NO 27
<211> LENGTH: 27
<212> TYPE: DNA
<213> ORGANISM: Artificial Sequence
<220> FEATURE:
<223> OTHER INFORMATION: primer

<400> SEQUENCE: 27
ttaatacgac tcactatagg ggaattg                                      27

<210> SEQ ID NO 28
<211> LENGTH: 25
<212> TYPE: DNA
<213> ORGANISM: Artificial Sequence
<220> FEATURE:
<223> OTHER INFORMATION: primer
```

-continued

```
<400> SEQUENCE: 28
ggttatgcta gttattgctc agcgg                                              25

<210> SEQ ID NO 29
<211> LENGTH: 9
<212> TYPE: PRT
<213> ORGANISM: Campylobacter sp.
<220> FEATURE:
<221> NAME/KEY: MISC_FEATURE
<222> LOCATION: (2)..(2)
<223> OTHER INFORMATION: Any amino acid
<220> FEATURE:
<221> NAME/KEY: MISC_FEATURE
<222> LOCATION: (6)..(6)
<223> OTHER INFORMATION: Any amino acid
<220> FEATURE:
<221> NAME/KEY: MISC_FEATURE
<222> LOCATION: (8)..(8)
<223> OTHER INFORMATION: Any amino acid
<300> PUBLICATION INFORMATION:
<301> AUTHORS: Silva E., Marques AR, Fialho AM, Granja AT, Sa-Correia I
<302> TITLE: Proteins encoded by Sphingomonas elodea ATCC 31461 rmlA and
       upgG genes, involved in gellan gum biosynthesis, exhibit both
       dTDP- and UDP-glucose pyrophosphorylase activities
<303> JOURNAL: Environ Microbiol
<304> VOLUME: 71
<306> PAGES: 4703-4712
<307> DATE: 2005
<313> RELEVANT RESIDUES IN SEQ ID NO: (1)..(9)
<300> PUBLICATION INFORMATION:
<301> AUTHORS: Silva E., Marques AR, Fialho AM, Granja AT, Sa-Correia I
<302> TITLE: Proteins encoded by Sphingomonas elodea ATCC 31461 rmlA and
       upgG genes, involved in gellan gum biosynthesis, exhibit both
       dTDP- and UDP-glucose pyrophosphorylase activities
<303> JOURNAL: Environ Microbiol
<304> VOLUME: 71
<306> PAGES: 4703-4712
<307> DATE: 2005
<313> RELEVANT RESIDUES IN SEQ ID NO: (1)..(9)

<400> SEQUENCE: 29

Gly Xaa Gly Thr Arg Xaa Pro Xaa Thr
1               5

<210> SEQ ID NO 30
<211> LENGTH: 4
<212> TYPE: PRT
<213> ORGANISM: Campylobacter sp.
<300> PUBLICATION INFORMATION:
<301> AUTHORS: Silva E, Marques AR, Fialho AM, Granja AT, Sa-Correia I
<302> TITLE: Proteins encoded by Sphingomonas elodea ATCC 31461 rmlA and
       ugpG genes, involved in gellan gum biosynthesis, exhibit both dTDP
       and UDP-glucose pyrophosphorylase activities
<303> JOURNAL: Environ Microbiol
<304> VOLUME: 71
<306> PAGES: 4703-4712
<307> DATE: 2005
<313> RELEVANT RESIDUES IN SEQ ID NO: (1)..(4)
<300> PUBLICATION INFORMATION:
<301> AUTHORS: Silva E, Marques AR, Fialho AM, Granja AT, Sa-Correia I
<302> TITLE: Proteins encoded by Sphingomonas elodea ATCC 31461 rmlA and
       ugpG genes, involved in gellan gum biosynthesis, exhibit both dTDP
       and UDP-glucose pyrophosphorylase activities
<303> JOURNAL: Environ Microbiol
<304> VOLUME: 71
<306> PAGES: 4703-4712
<307> DATE: 2005
<313> RELEVANT RESIDUES IN SEQ ID NO: (1)..(4)

<400> SEQUENCE: 30

Glu Glu Lys Pro
1
```